United States Patent [19]
Riley et al.

[11] Patent Number: 5,811,538
[45] Date of Patent: Sep. 22, 1998

[54] PROCESS FOR THE PURIFICATION OF OLIGOMERS

[75] Inventors: Timothy Andrew Riley, Nipomo; Mark Alan Reynolds, San Diego; Lloyd Robert Snyder, Orinda; Robert E. Klem, Rancho Santa Fe, all of Calif.

[73] Assignee: Genta, Incorporated, San Diego, Calif.

[21] Appl. No.: 367,069

[22] Filed: Dec. 30, 1994

Related U.S. Application Data

[63] Continuation-in-part of Ser. No. 176,851, Dec. 30, 1993, abandoned.

[51] Int. Cl.⁶ ............................. C12P 19/34; C08G 69/26
[52] U.S. Cl. ......................... 536/25.4; 528/332; 424/486
[58] Field of Search ........................... 536/25.4; 424/486; 528/332

[56] References Cited

U.S. PATENT DOCUMENTS 5,342,931   8/1994   Woodard ................................. 536/25.4

OTHER PUBLICATIONS

Agrawal et al.,*Chemical Abstracts, 113:317(2)* abstract No. 128809q, *Journal of Chromatography,* 509:396ff(990) (see entire abstract).

Jerald L. Hoffman, *J. Macromolecular Science and Chemistry,* A7(5), pp. 1147–1157 (1973).

*Primary Examiner*—Gary L. Kunz
*Attorney, Agent, or Firm*—Knobbe, Martens, Olson & Bear, LLP

[57] ABSTRACT

Methods for purifying an oligomer by normal phase column chromatography on a support selected from polyhydroxyethyl aspartamide, hydrophilic silica and silica from an oligomer impurity having a different nucleoside sequence are described. These methods are based upon the different retention times of the oligomer and the impurity on the column.

31 Claims, 18 Drawing Sheets

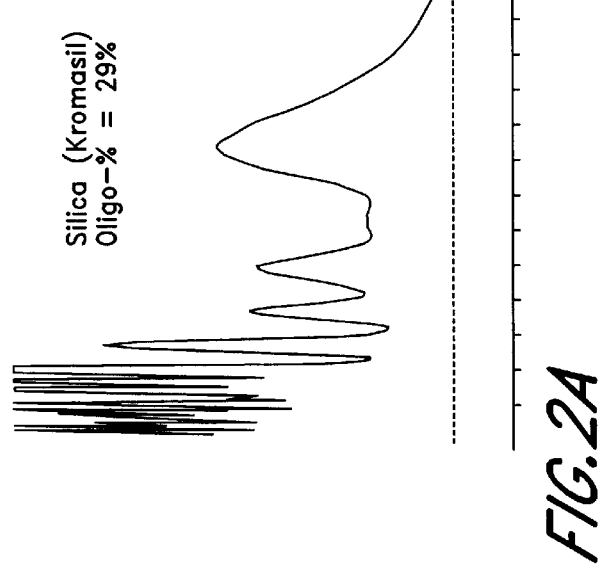
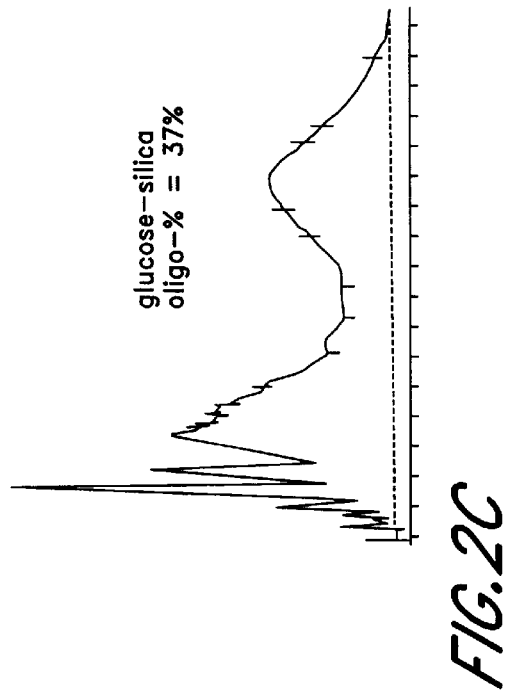
FIG.2A  FIG.2B  FIG.2C  FIG.2D

PROCESS FOR THE PURIFICATION OF OLIGOMERS

RELATED APPLICATIONS

This application is a continuation-in-part of commonly assigned U.S. patent application Ser. No. 08/176,851 filed Dec. 30, 1993, now abandoned, the disclosure of which is incorporated herein by reference.

BACKGROUND OF THE INVENTION

The present invention is directed towards improved processes for purifying oligomers. These processes are particularly useful for purifying all-methylphosphonate oligomers.

An oligomer is comprised of two or more nucleotides. Generally, the nucleotides are either adenine, thymine, guanine, cytosine, or uracil. A given nucleotide can hydrogen bond with its complementary nucleotide. Adenine can hydrogen bond with thymine or uracil. Guanine can hydrogen bond with cytosine.

An oligomer can selectively hybridize to its complementary oligomer. Oligomers have various uses based upon selective hybridization, including use as hybridization probes, amplification primers and targeted chemotherapeutic agents. See, Zon, in *HIGH PERFORMANCE LIQUID CHROMATOGRAPHY IN BIOTECHNOLOGY*, 301–397, Wiley-Interscience, New York, (W. S. Hancock, ed, 1990).

Oligomers containing 3'–5' phosphodiester linkages as well as modified 3'–5' linkages have been claimed to be effective therapeutic agents able to enter cells and hybridize with a complementary nucleotide sequence. See, Kaji, U.S. Pat. No. 4,689,320; Tullis, U.S. Pat. No. 5,023,243; Catin et al., U.S. Pat. No. 5,110,802 (not admitted to be prior art); and Goodchild et al., U.S. Pat. No. 4,806,463.

Several procedures are available to synthesize oligomers having 3'–5' phosphodiester linkages as well as modified 3'–5' linkages. These procedures include solid phase synthesis by the "Phosphite-Triester Method," Atkinson and Smith, *OLIGONUCLEOTIDE SYNTHESIS*, IRL Press (Gait ed. 1984); synthesizing methylphosphonate oligomers using a polystyrene support, Miller, et al. *Nucleic Acids Res.* 11:6625 (1983); and a procedure using low water oxidizer reagents, Klem et al., entitled "Improved Process For The Synthesis Of Oligomers," PCT WO92/07864.

Several procedures are available to purify synthesized oligomers by separating a fully synthesized oligomer from the various impurities which may arise during synthesis. See, Zon and Thompson, *BioChromatography* 1:22 (1986). These procedures include polyacrylamide gel electrophoresis (PAGE), silica-based anion-exchange chromatography, polymer-based anion exchange chromatography, silica-based reverse phase chromatography, and polymer-based reverse phase chromatography.

Zon, supra in *HIGH PERFORMANCE LIQUID CHROMATOGRAPHY IN BIOTECHNOLOGY*, reviews various procedures for purifying oligomers and points out deficiencies in these procedures. According to Zon, PAGE is relatively time consuming, labor intensive and provides a low yield of usable DNA; polymer-based anion-exchange chromatography require "tedious methods" to eliminate contaminating reagents, and insure column performance and long life; silica-based anion-exchange chromatography (e.g., SAX) involves the use of time-consuming gradients, high concentration of eluting anion, short column life, and strong retention. Anion exchange chromatography cannot be used to separate all-methylphosphonates, because these oligomers are not charged.

SUMMARY OF THE INVENTION

The present invention is directed towards improved methods for purifying oligomers using normal phase chromatography. In particular, a column using normal phase supports such as bare silica, hydrophilic silica or polyhydroxy aspartamide (such as HILIC™) is used to separate oligomers from oligomer impurities differing in the number of nucleotide amino groups. Thus, these methods are especially useful for purifying oligomers independent of a charged internucleosidyl linkage which joins the individual nucleosides making up the oligomer. However, these methods also are suitable for purifying oligomers having charged internucleosidyl linkages. Such charged linkages include phosphodiester, phosphorothioate and phosphorodithioate linkages. These methods are especially suited to separating full length oligomers from full line sequences. These methods are particularly useful for purifying all-methylphosphonate oligomers and other neutral oligomers.

Advantages of purifying oligomers using the methods of the present invention over other procedures include the ability to obtain higher yields than PAGE and the improved purification obtained of crude mixtures of oligomers, including neutral oligomers compared to reverse phase chromatography.

Thus, the present invention is directed to methods of separating an oligomer having a selected nucleoside sequence from an oligomer impurity having a different nucleoside sequence by normal phase column chromatography on a column having a support selected from polyhydroxyethyl aspartamide, silica and hydrophilic silica, including separation conditions selected so that the oligomer has a different retention time on the column than the oligomer impurity. The present method is especially suited to separating the oligomer from oligomer purities having fewer nucleosides such as sequence failures, and also especially from oligomer impurities having a different number of nucleoside amino groups, optionally, the separated oligomer may be subjected to a further step on a reverse phase column if oligomer impurities which are amino deletions are thought to be present. According to one aspect, these methods are particularly useful for purifying oligomers which are substantially neutral, especially methylphosphonate oligomers.

According to one aspect the oligomer to be purified has internucleosidyl linkages which may be phosphodiester, phosphorothioate, phosphorodithioate, methylphosphonothioate and methylphosphonate linkages. According to a preferred aspect, the oligomer has at least one 2'-O-methyl nucleoside, more preferably, all the nucleosides are 2'-O-methyl nucleosides.

According to an alternate aspect the oligomer to be purified has methylphosphonate or methylphosphonothioate linkages which are mixed with non-phosphonate internucleosidyl linkages selected from phoshodiester, phosphorothioate and phosphorodithioate linkages. Such oligomers include oligomers wherein the methylphosphonate or methylphosphonothioate linkages are interspersed with non-phosphonate linkages in a ratio of from 1 non-phosphonate linkage to about 1 methylphosphonate or methylphosphonothioate linkage to 1 non-phosphonate linkage to about 4 methylphosphonate or methylphosphonothioate linkages and, further, include oligomers wherein such linkages are alternating. Alternatively, such oligomers include oligomers having a block of consecutive non-phosphonate linkages; these oligomers may have a majority of non-phosphonate linkages, including charged linkages such as phosphodiester and phosphorothioate linkages. These oligomers include oligomers having a block of consecutive non-phosphonate linkages more preferably of 5 to 9 nucleosides and at either or both of the 5'- and 3'-end of the block having consecutive methylphosphonate or methylphosphonothioate linkages or alternatively having consecutive alternating methylphosphonate (or methylphosphonothioate) and non-phosphonate linkages. Oligomers having other permutations and combinations of these linkages than those expressly described herein and set forth in the Examples may be purified according to the methods of the present invention and their purification is considered to be within its scope. These methods also may be used to purify oligomers which are a conjugate between an oligonucleoside (including all the above constructions) and a conjugation partner.

In a preferred aspect, a process is disclosed for the purification of an oligomer to be purified from an oligomer impurity having a different nucleoside sequence using silica chromatography. The purification is based upon the difference in retention time of the oligomer from an oligomer impurity on silica. The retention time is a function of retention strength (of oligomer or impurity by silica). The stronger the retention strength the longer the retention time. The weaker the retention strength the shorter the retention time.

Both bare silica and silica having a suitable hydrophilic moiety attached thereto may be used to purify oligomers. Suitable hydrophilic moieties include cyclodextrin, glucose, glycidoxypropyl and diol groups. An appropriate hydrophilic moiety, may decrease, but does not prohibit interaction between silica silanol groups and nucleoside amino groups.

In a preferred embodiment, a retention time is chosen which corresponds to a capacity factor (k') greater than 5. The capacity factor is directly related to the retention time. This relationship is described by relationship $$k'=(t_r-t_o)/t_o; \text{ or} \qquad (1)$$

$$t_r=(k')(t_o)+(t_o). \qquad (2)$$

wherein $t_r$ is retention time. As retention time increases separation of fully synthesized oligomers from impurities increases and then levels off.

In a more preferred embodiment, chromatography conditions are selected so that the capacity factor is between 5 and 10. A retention time corresponding to a capacity factor between 5 and 10 has been found to give time efficient separation of a fully synthesized oligomer from impurities. A shorter retention time was found to result in less separation of fully synthesized oligomer from impurities. On the other hand, a longer retention time resulted in little additional purification at the expense of additional time.

The retention time is affected by different factors, including the following: (1) the oligomer composition (e.g., the number of amino groups and the number of ionic linkages); (2) column factors and (3) separation conditions.

Two effects of the oligomer composition on retention time are caused by the presence of ionic groups and the nucleotide composition. Oligomers containing ionic linkages have a weaker retention on silica than oligomers containing neutral linkages. Generally, the more nucleotide amino groups present, the longer the retention time on silica. Retention of neutral oligomers (e.g., all-methylphosphonates), was found to increase as the number of nucleotide amino groups increased. Retention of ionic oligomers (e.g., all-phosphorothioates) generally increased as the number of nucleotide amino groups increased. In contrast, 5'-mono-diester methylphosphonate oligomers generally elute before the (n–1)-mer which has lost its charged diester. This latter effect appears to be due to repulsion between ionic linkages and non-protonated silanol groups.

Column factors include the characteristics of the silica used, column length, column diameter, and flow rate. A column length or column diameter increases, or as the flow rate decreases, retention increases. A the surface area of the silica increases, retention increases. The surface area of the silica is preferably greater than 100 m²/g, more preferably between 100–400 m²/g.

Separation conditions affecting retention time include the temperature, the mobile phase Ph, and the mobile phase composition. The mobile phase is composed of an organic solvent and an aqueous buffer. As the percentage of organic solvent in the mobile phase increases, retention time increases. The mobile phase preferably comprises 30% to 70% acetonitrile and 70% to 30% aqueous buffer. The ion concentration of the aqueous buffer is preferably between 2–100 mM. As the ion concentration of the aqueous buffer increases, retention time of an all-methylphosphonate oligomer decreases, while retention of an oligomer with one or more diester or phosphorothioate linkages increases. Preferably, ammonium acetate is used as the aqueous buffer.

In another preferred embodiment, an amino-deletion impurity or failure sequence is separated from its corresponding fully synthesized oligomer using reversed phase chromatography. Thus, in this preferred embodiment two purification steps are carried out. The first uses silica chromatography; the second uses reverse-phase chromatography.

In another aspect, a process is described for purifying oligomers by adjusting purification conditions to establish a desired retention time for a given oligomer. An approximate initial retention time for the oligomer product can be estimated or a desired change in retention time can be predicted by use of general relationships as described herein. Establishing a retention time is achieved by first selecting a reference condition having a particular set of column factors and separation conditions. In a second step, relationships describing the effect on retention time by varying one or more of the separation conditions are derived by measuring the retention time of oligomers under the varied separation conditions. In a third step, the derived relationships are used to either predict or establish a retention time of an oligomer. Preferably, the retention time is predicted or established for oligomers having 3'–5', or 2'–5' linkages which are phosphodiester, phosphorothioate, phosphorodithioate, or methylphosphonate linkages. More preferably, the purified oligomer has 3'–5' linkages. Especially preferred are oligomers having methylphosphonate or phosphodiester linkages.

In a preferred embodiment, the reference conditions include using a 25×0.46 cm Nucleosil silica column, a mobile phase of 50% acetonitrile/aqueous buffer, where the aqueous buffer is 2.0 mM ammonium acetate pH 6.0, a temperature of 50° C., and a flow rate of 1 ml/minute. These reference conditions are based on small-scale studies. As described below, for larger scale purification the preferred column size could be wider and longer.

In a more preferred embodiment the mobile phase is changed from 50% acetonitrile/aqueous to either a greater or a lesser percentage of buffer to help establish or predict a retention time based on the following relationships: relationship:

$$\Sigma R_i = [\Sigma R_{i(50)}][f(\% B)] \qquad (8):$$

wherein % B refers to the percentage of acetonitrile and $[\Sigma R_{i(50)}]$ refers to relationship $$\Sigma R_f = 0.090\ g + 0.155\ a + 0.140\ c - 1.00\ d \qquad (4):$$

obtained under reference conditions where "g" refers to the number of guanine nucleotides, "a" refers to the number of adenine nucleotides, "c" refers to the number of cytosine nucleotides, "d" refers to the number of diester groups; and f(% B) is found based upon either relationship (9) to be used when % B ≧ 61% and to comprise:

$$f(\%\ B) = 10^{0.018(\%\ B \cdot 50)}$$

or relationship (10) to be used when % B<61% and to comprise:

$$f(\%\ B) = 2.9 - 0.113(\%\ B) + 0.0015(\%\ B)^2.$$

In another more preferred embodiment, the buffer concentration is changed from 2.0 mM to aid in establishing or predicting the retention time based relationship $$\log k_{50} = -0.64 + [\Sigma R_{i(50)}][f(\%\ B)] - d - 0.00021(g+a+c)(C-2) + 0.14d$$
$$\log (C)(0.01) - 0.105d \qquad (11):$$

where $k_{50}$ is the k' at 50° C.; "C" is the buffer ion concentration in mM, when the buffer ion concentration is equal to or greater than 50 mM "C" is set at 50 mM; and the other terms are defined as described above.

In another more preferred embodiment, the temperature is changed from 50° C. to help establish or predict the retention time based upon relationship $$\log k' = (\log k_{50}) - B[(1/273) - 1/T)] \qquad (12):$$

and B is determined using relationship $$B = (950 \log k_{50}) + 540 \qquad (13):$$

T is the temperature in ° K. (273+temperature in ° C.), log $k_{50}$ refers to log k' at reference condition (50° C.), and k' refers to the value of k' at the new temperature.

Other features and advantages of the invention will be apparent from the following description of the detailed description thereof, and from the claims.

BRIEF DESCRIPTION OF THE DRAWINGS

FIGS. 2A to 2D, depict chromatograms demonstrating the purification of an all-methylphosphonate oligomer, TP-579, on (2A) Kromasil, (2B) Cyclobond, (2C) glucose-silica, and (2D) diol-silica.

DEFINITIONS

Figure 1A:
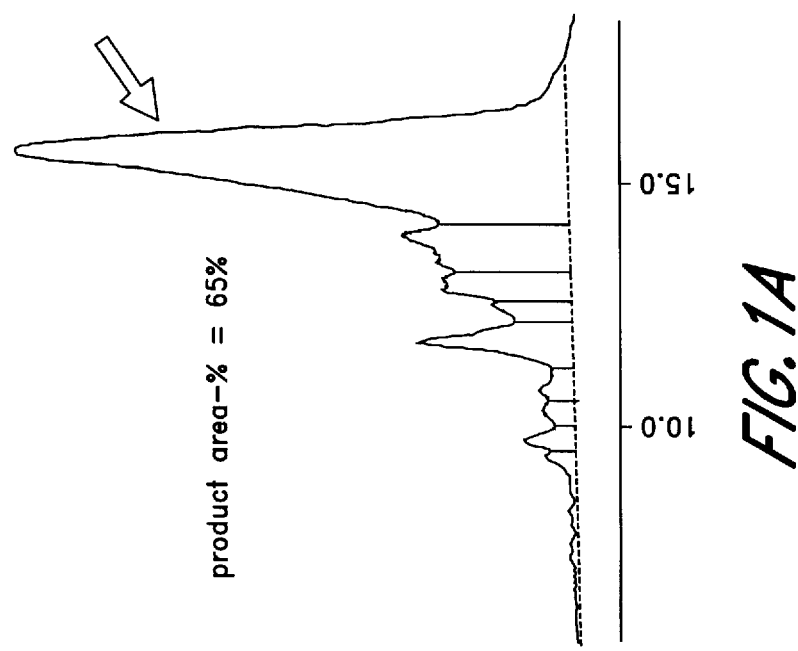
FIGS. 1A and 1B, depict chromatograms demonstrating the purification of an all-methylphosphonate oligomer, TP-579, on (1A) Whatman C18 (25×0.46 cm) 10–25% acetonitrile/water gradient in 15 minutes, 1.0 ml/minute at 30° C.; and (1B) Kromasil (silica column) (25×0.46 cm), 50% V acetonitrile/buffer (50 mM potassium acetate, pH 6.0, 1.0 ml/minute, at 50° C.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-analogs such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "phosphonate" refers to the group

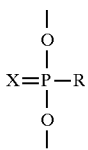

wherein X is oxygen or sulfur, R is hydrogen or an alkyl or aryl group, and thus includes various example of phosphonate and phosphonothioate internucleosidyl linkages. Suitable alkyl or aryl groups include those which do not sterically hinder the phosphonate linkage or interact with each other. The phosphonate group may exist in either an "R" or an "S" configuration. Phosphonate groups may be used as internucleosidyl linkages (or links) to connect nucleosidyl unit or a ucleosidyl unit and a non-nucleosidy monomeric unit. The term "lower alkylphosphonate" refers to groups where X is oxygen and R is lower alkyl of 1 to 3 carbon atoms. "Methylphosphonate" refers to groups where X is oxygen and R is methyl. The term "phosphonothioate" refers to those groups where X is sulfur. The term "lower alkylphosphonothioate" refers to groups where X is sulfur and R is lower alkyl of 1 to 3 carbon atoms. The term "methylphosphonothioate" refers to a phosphonothioate group wherein R is methyl.

The term "phosphodiester" or "diester" refers to the group

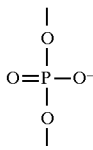

wherein phosphodiester groups may be used as internucleosidyl phosphorus group linkages (or links) to connect nucleosidyl units.

The term "oligonucleoside" or "Oligomer" refers to two (2) or more nucleotides covalently linked by internucleosidyl linkages, that is a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides. The term also includes oligonucleosides wherein one or more of the phosphorus group linkages between monomeric units has been replaced by a non-phosphorous linkage such as a formacetal linkage, a thioformacetal linkage, a sulfamate linkage, or a carbamate linkage. It also includes oligonucleosides wherein both the sugar and the phosphorous moiety have been replaced or modified such as morpholino base analogs, or polyamide base analogs. Optionally, a nucleoside moiety may serve to link other small molecules which may interact with target sequences or alter uptake into target cells.

The term "neutral Oligomer" refers to oligomers which have nonionic internucleosidyl linkages between nucleoside monomers (i.e., linkages having no positive or negative ionic charge) and include, for example, Oligomers having internucleosidyl linkages such as alkyl- or or aryl- phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, and carbamate linkages. Optionally, a neutral Oligomer may comprise a conjugate between an oligonucleoside and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside and the resulting oligomer conjugate be substantially neutral.

The term "substantially neutral" in referring to an Oligomer refers to those Oligomers in which at least about 80 percent of the internucleosidyl linkages between the nucleoside monomers are nonionic linkages.

The term "acid resistant" refers to Oligomers which are resistant, in comparison to deoxyribooligo- nucleotides, to acid-catalyzed depurination by hydrolysis of the N-glycosyl bond.

"All-diester oligomer" refers to an oligomer wherein all the internucleosidyl linkages are joined by 3'–5' phosphodiester linkages.

"All-methylphosphonate oligomer" refers to an oligomer wherein all the internucleosidyl linkages are 3'–5' methylphosphonate linkages.

"All-phosphorothioate oligomer" refers to an oligomer wherein all the internucleosidyl linkages are 3'–5' phosphorothioate linkages.

"Amino-deletion" refers to an impurity of a fully synthesized oligomer, wherein the impurity has the same number of nucleotide amino groups but has less total number of nucleotides (e.g., the fully synthesized oligomer differs from the impurity by a thymine or uracil).

"5'-diester-methylphosphonate oligomer" refers to an oligomer having all methylphosphonate internucleosidyl linkages except for a internucleosidyl linkage diester at the 5'-end of the oligomer.

"Ionic oligomer" refers to an oligomer comprised of ionic internucleosidyl linkages (e.g., phosphodiester and phosphorothioate or phosphorodithioate) internucleosidyl linkages.

"Fully synthesized oligomer" refers to an oligomer synthesized properly so as to have the full-length nucleoside base sequence (e.g., no missing sequences or chemically degraded nucleotides).

"Internucleosidyl linkages" refers connecting groups between nucleosides.

"Mixed diester-methylphosphonate oligomer" refers to an oligomer wherein the nucleosides are joined by 3'–5' internucleosidyl linkages, where one or more of the internucleosidyl linkages is a methylphosphonate linkage and one or more of the internucleosidyl linkages is a phosphodiester linkage.

"Mixed ionic-neutral oligomer" refers to an oligomer having one or more ionic internucleosidyl linkages and one or more neutral internucleosidyl linkages.

"Modified internucleosidyl linkage" refers to a linkage other than a 3'–5' phosphodiester internucleosidyl linkage.

"2'-O-methyl" nucleosides are ribose-based nucleosides wherein the 2'-OH of the ribose moiety is replaced with a 2-OCH$_3$.

"Silica" refers to bare silica or hydrophilic silica. Bare silica lacks an attached moiety. Hydrophilic silica, has an attached hydrophilic moiety.

Relationships $$k'=(t_r-t_o)/t_o \qquad (1)$$

$$t_r=(k')(t_o)+(t_o) \qquad (2)$$

$$\log k'=A+\Sigma R_{i(50)} \qquad (3)$$

$$\Sigma R_{i(50)}=0.090\ g+0.155\ a+0.140\ c-1.00\ d \qquad (4)$$

$$t_o=V_m/F \qquad (5)$$

$$\text{(all-MP)}\ V_m=(0.5)(L)(d_c^2) \qquad (6)$$

$$\text{(Diester)}\ V_m=(0.36)(L)(d_c^2) \qquad (7)$$

$$\Sigma R_i=[\Sigma R_{i(50)}][f(\% B)] \qquad (8)$$

$$\text{(for \% B>61\%)}\ f(\% B)=10^{0.018(\% B-50)} \qquad (9)$$

$$\text{(for \% B<61\%)}\ f(\% B)=2.9-0.113(\% B)+0.0015(\% B)^2 \qquad (10)$$

$$\log k_{50}=-0.64+[\Sigma R_{i(50)}][f(\% B)]-d-0.00021(g+a+c)(C-2)+0.14d\ \log (C)(0.01)-0.105d \qquad (11)$$

$$\log k'=(\log k_{50})-B[(1/273)-1/T)] \qquad (12)$$

$$B=(950\ \log k_{50})+540 \qquad (13)$$

Terms used in the above relationships
$t_r$=band retention time
$t_o$=column dead time
k'=capacity factor
$k_{50}$=capacity factor at reference conditions
A=constant for a particular column (depending on the surface area)
g=guanine
a=adenine
c=cytosine
d=diester
F=flow rate
L=column length in cm
$d_c$=column internal diameter in cm
$\Sigma R_i$=nucleotide interaction
$\Sigma R_{i(50)}$=nucleotide interaction under reference conditions %
B=mobile phase composition of acetonitrile/aqueous buffer
f=a function of % B as described in relationships (9) and (10)
C=buffer ion concentration in mM, if "C" is equal to 50 mM when the buffer ion concentration is 50 mM or more
T=temperature in ° K.

DETAILED DESCRIPTION OF THE INVENTION

The present invention features methods using silica to purify oligomers. The described methods are characterized by hydrogen bonding between nucleotide amino groups and silanol groups. These methods are particularly useful to purify neutral oligomers such as all methylphosphonate oligomers from impurities which may arise during oligomer synthesis. Also described are methods of purifying fully synthesized oligomers wherein the retention time of a fully synthesized oligomer is established or predicted thereby facilitating the purification of a fully synthesized oligomer.

Impurities such as sequence failures, atypical sequences, and chemically modified or degraded nucleosides may arise during oligomer synthesis. See, Zon, HIGH PERFORMANCE LIQUID CHROMATOGRAPHY IN BIOTECHNOLOGY, 301–397, (1990). Sequence failures occur when one or more 3'-terminal nucleosides are not coupled to the growing nucleoside chain. Atypical sequences are those sequences which arise when a nucleoside is not coupled to the growing nucleoside chain during one of the intermediate synthesis cycles and during a subsequent synthesis cycle a subsequent nucleoside is coupled. An atypical sequence is thus basically an internal deletion. Examples of chemical modification or degradation products include oligomers having nucleosides which have undergone deamination or depurination.

Impurities arising during synthesis of an oligomer often differ in the number of nucleoside amino groups present from a fully synthesized oligomer. For instance, an atypical sequence or sequence failure will have a decreased number of nucleosides. Oligomers having fewer nucleosides than a fully synthesized oligomer will have fewer nucleotide amino groups unless the missing nucleoside is thymine or uracil. Similarly, chemically modified or degraded nucleosides wherein a nucleoside amino group is altered will have fewer nucleoside amino groups. An oligomer having fewer nucleoside amino groups is retained on silica to a different extent than a properly (or fully) synthesized oligomer having a complete nucleoside sequence.

Generally, a significant problem in the synthesis of oligomers is the failure of the last nucleoside to be coupled. If the last nucleoside is either uracil or thymine, this particular impurity will not be separated from a fully synthesized oligomer on silica. This problem can be avoided by designing the oligomer so the last residue is not uracil or thymine, or having an additional purification step comprising reverse phase chromatography.

Separation Mechanism

The present invention discloses the use of silica to purify oligomers. Previously used chromatograpic methods, such as reverse phase and anion-exchange chromatography, were carried out using a moiety attached to silica (bonded phase silica). The attached moiety to silica was chosen to interact with an oligomer. Moieties used included non-ionic groups such as octadecysilyl (C-18) which provided a hydrophobic matrix for reverse phase chromatography; and anionic groups such as amines which provided a polar group for ion exchange chromatography. See, McLaughlin et al., OLIGONUCLEOTIDE SYNTHESIS, IRL Press (Gait ed. 1984). According to McLaughlin et al., supra, "anion-exchange chromatography resolution is related to the number of phosphate groups present." Thus, with anion-exchange chromatography, oligomers were retained by interactions between phosphate groups of the internucleosidyl linkages and the bonded support, rather than between nucleoside amino groups and silica.

In discussing bonded phase silica chromatography, McLaughlin et al., advocated the use of Hypersil (Shandon, Southern Co, Runcorn, UK) McLaughlin pointed out, as an advantage of Hypersil, that ". . . the support is capped, such that there should be no influence of (Si—OH) groups on the separation mechanisms." McLaughlin et al., supra, at p. 119.

In contrast, Applicants have found that silanol groups (Si—OH) rather than hindering purification, provide a basis for purification of oligomers by interacting with nucleoside amino groups. Based upon the results observed with 3'–5' oligomers, these interactions should work to separate other molecules containing a different number of nucleoside amino groups. Purification is characterized by hydrogen bonding between silanol groups on the surface of the silica and nucleoside amino groups. Thus, it is important that nucleoside amino groups be able to interact with silica silanol groups. Such interactions can occur if using either bare silica or hydrophilic silica to achieve purification according to the muthods of the present invention.

Oligomers were successfully purified using silica having attached hydrophilic moieties as large as cyclodextrin; however the use of silica with cyclodextrin attached resulted in weaker retention. Hydrophilic silica is preferably used to speed up purification of oligomers strongly retained by silica.

Appropriate hydrophilic silica supports, other than those described herein, may be determined by one skilled in the art. This determination can be made by measuring the ability of a particular silica modified with hydrophilic moieties to prevent hydrogen bonding between nucleoside amino groups and silanol groups. For example, such a determination can be made by measuring the retention time of a fully synthesized oligomer and different sequence failures. The retention time of two types of sequence failures should be compared with the retention time of the fully synthesized oligomer One type of sequence failure should be an amino-deletion such as replacement of C by T or U. The second type, a sequence failure, should differ in the number of nucleoside amino groups from the fully synthesized oligomer. If separation is occurring by hydrogen bonding between nucleoside amino groups and silanol groups, the amino-deletion will have a similar retention time as the fully synthesized oligomer and the second type of sequence failure will have a substantially shorter retention time than the fully synthesized oligomer.

Our finding of the ability of silica to separate oligomers based upon the number of nucleoside amino groups has been evidenced by several observations. Of particular importance are our observations regarding retention of sequence failures, amino-deletions and the effect of different pH. For a given oligomer, retention time generally decreases as the number of sequence failures increases if the deleted nucleoside or nucleosides from the oligomer are not thymine or uracil. Oligomers having thymine or uracil deletions in a particular oligomer sequence will be retained to the same extent as the fully synthesized oligomer.

We have observed two pH effects when the pH is lowered from about 7 to about 2. First, as the pH approaches 4 oligomer retention time increases. As the pH is lowered from 7 to 4 protonation of silanol groups is belived to increase (estimated $pK_a$ for silanol is≈7). The protonated silanol groups can retain oligomers by hydrogen bonding to nucleoside amino groups. However, as the pH is lowered further, from about 4 to 2, the retention time decreases. At lower pH's nucleoside amino groups become protonated. Adenine 1-N has a pKa of 3.5, guanine 7-N has a $pK_a$ of 2.5, and cytosine 3-N has a $pK_a$ of 4.2. The protonation of both the nucleoside amino groups and the silanol groups may decrease hydrogen bond formation.

These pH effects we observe with our purification methods are inconsistent with retention occurring by an ion exchange mechanism. As pH is decreased from 7 to 4 the silanol groups are losing their negative charge due to protonation. Thus, the silanol groups would be expected to have an decreased interaction with oligomers if retention was occurring by an ion exchange mechanism. However, we have observed that as the pH decreased from about pH 7 to about pH 4 retention of oligomers increased. Furthermore, if oligomers were retained by an ion exchange mechanism, protonation of nucleoside amino groups of the oligomers would be expected to result in increased retention. However, we have observed that as the pH is decreased below about pH 4, oligomer retention decreases. Thus, with the methods of the present invention, opposite effects are observed with decreased pH.

Type of Oligomer

Both the oligomer nucleoside base composition and the presence of ionic groups affects retention of the oligomer on silica. Generally, the retention strength of oligomers having the same number of ionic groups increases as the number of nucleoside amino groups increases. Retention of neutral oligomers (e.g., all-methyophosphonates), was found to increase as the number of nucleoside amino groups increased. Two oligomers of different sizes which have the same number of adenine, cytosine, and guanine group, were found not to be adequately separated on silica. Oligomers of various sizes may be purified on silica. Preferably the oligomer to be purified is between 5 and 50 nucleosides in length, more preferably the oligomer is between 10 and 30 nucleosides in length.

Both the number and type of ionic linkages affect retention of the oligomer on silica. As the number of ionic linkages increases, retention decreases. Decreased retention may be due to repulsion of negatively charged linkages by negatively charged silanol groups. As the pH is lowered to about 4, retention increases for oligomers having ionic linkages. For ionic and mixed-ionic oligomers purification is preferably performed at a lower pH (e.g., pH 4). However, the use of lower pH, while increasing retention, will also decrease solubility.

We have found that all-diester oligomers and all-phosphorothioate oligomers need compensating conditions which may include the use of a lower pH to obtain good separation on silica. The conditions used to obtain good separation were found to decrease the sample solubility. In addition, we found the elution profile of ionic oligomers on silica was different than for neutral oligomers. For example, a band (thought to be the n-1 sequence failure band) in the elution profile of certain all-diester oligomers and all-phosphorothioate oligomers was observed to exhibit a longer retention time than the fully synthesized oligomer. Despite the altered profile, satisfactory separation of all-diester oligomers and all-phosphorothioate oligomers were obtained using silica.

All-phosphorothioate oligomers are retained less than all-diester oligomers and are more difficult to separate on silica than are all-diester oligomers. The lesser retention may be due to the greater acidity of a phosphorothioate linkage over a phosphodiester linkage. The greater acidity of a phosphorothioate linkage may cause the phosphorothioate linkage to be more difficult to protonate than a phosphodiester linkages. Consequently, an oligomer containing phosphorothioate linkages has more negative charge than an oligomer having the same sequence and number of phosphodiester linkages at a lower pH.

Good separation was achieved for an all-phosphorothioate oligomer using silica chromatography at a pH of 4.0, using 13% acetonitrile, and a temperature of 23° C. These conditions decreased the solubility of the all-phosphorothioate to about 0.5 mg/mL. Because of decreased sample solubility using compensating conditions to purify all-phosphorothioate oligomers, separation of all-phosphorothioate oligomers on silica is more suited for oligomers 18 nucleosides or less.

Silica

We have found that a number of different types of bare silica and hydrophilic silica are suitable for purifying oligomers according to the methods of the present invention.

Suitable bare silica for use in these methods includes those sold under the trade-names Kromasil, Vydac TP and HS, Nucleosil, and PQ. We have found that these silica products provided purification of a given all-methylphosphonate oligomer.

Separations equivalent to those obtained using bare silica columns can be obtained using columns in which a hydrophilic moiety is attached to the silica. The use of hydrophilic silica requires adjusting separation conditions to compensate for the weaker retention. Examples of useful hydrophilic moieties include; α-, β, or γ-cyclodextrin, glucose, diol, glycidoxypropyl and like hydrophilic moieties. Columns using silica bonded to either alkyl (-C8, -C18) or cyanoalkyl (-c3-CN) groups gave unsatisfactory purification of oligomers.

Silica Characteristics

Characteristics of the silica particles used in a column affects retention time of an oligomer. These characteristics which include, surface area, pore diameter, and particle size, affect the number of silanol groups available to interact with nucleoside amino groups. Generally, availability of a larger number of silanol groups will result in more interactions with the nucleoside amino groups and stronger retention, and, thus, longer retention time.

Preferably, silica is used having characteristics which result in a stronger retention and help achieve a capacity factor between 5 and 10. The use of silica having a weaker retention may require adjusting separation conditions to increase retention. The adjustments to these conditions, such as lowering the operating temperature, decreasing the pH, or increasing the percentage of acetonitrile concentration in the mobile phase, may cause a decrease in sample solubility, thereby preventing the separation of larger samples.

Silicas of higher surface area are preferred. Preferably the silica has a surface area greater than 150 $m^2/g$. Use of silica of lower surface area results in decreased retention time, may limit the weight of sample that can be separated, regardless of sample solubility, and may call for the use of separation conditions which increase retention time but decrease oligomer solubility.

Preferably, the silica used according to the methods of the present invention has a pore diameter equal to or greater than 10 nm. Silica having pore diameters less than 10 nm have a decreased column efficiency (plate number) which may require the use of longer columns and/or lower flow rates. These changes in conditions resulted in a decreased sample throughout measured in grams of sample/hr.

Silica particle size is preferably 3 $\mu$m or larger. As particle size increases, the efficiency of the particles to bind oligomers decreases. Larger particles, 10–50 $\mu$m, are preferred for large-scale separations [e.g., those involving longer and wider columns]. When using larger particles it may be necessary to increase column length or reduce flow rate to compensate for the lower efficiency of large particles.

Comparison Of Purification Columns

Purifications of various oligomers were performed using various type of purification columns including bare silica, hydrophilic-bonded silica, reverse phase columns, and anionic exchange columns used according to the methods of the present invention. Overall, silica columns were found to be more efficient (i.e., gave better separations) than the other columns tested. Silica columns were more efficient at purifying crude preparations of all-methylphosphonate oligomers and 2'-O-methylphosphonate oligomers, than reverse phase columns. Ion exchange columns cannot be used to separate all-methylphosphonate oligomers. Silica columns were found to be as efficient as reverse phase columns in purifying all-diester oligomers and low concentrations of all-phosphorothioate oligomers.

Purification of impure all-methylphosphonate oligomers using silica columns was compared to purification using different reverse phase columns. The columns tested included columns packed with particles made of polystyrene, alkyl-silica, and cyanopropyl-silica. The quality of the separations were assessed according to the fractional product area. The fractional product area is the area under a product band divided by the total area under the impurities plus product bands. A small fractional product area indicates that most impurities have separated from the desired product and signifies a more pure sample. Using crude oligomers (about 30% pure), the fractional product area for the tested reverse phase columns varied from about 64–70%, while the fractional product area for silica columns tested was about 30%.

Silica columns can be used for analytical and preparative purification of oligomers. Successful purification using 10–15 mg of an all-methylphosphonate oligomer on a 25×0.46 silica column was obtained. Such purification can be scaled up for larger samples by increasing the diameter and length of the column. When column length L and column diameter d are increased by factors x and y, the amount of sample charged to the column can be increased by $xy^2$.

As mentioned above, oligomers differing only in nucleosides lacking an amino group are not expected to be separated on silica. Thus, an additional step involving reverse phase chromatography is necessary to purify fully synthesized oligomers from amino-deletions. This additional step is recommended if the n-1 residue is either thymine or uracil.

Preferred Purification On Silica

Purification on silica is optimized by determining the preferred retention time for purifying an oligomer on a particular column. The procedures disclosed herein determine the preferred retention time based upon the capacity factor for a given column. Capacity factor and retention time are related as described in relationships (1) and (2). The most preferred retention time provides for time efficient purification. We have determined that since the preferred capacity factor is greater than 5, preferred retention times will give such a capacity factor. More preferably the retention time corresponds to a capacity factor between 5 and 10.

Illustrative of the present invention, the preferred capacity factor was determined using the all-methylphosphonate oligomer TP-579. As described in Example 4, as retention time increased, product purity increased. At a retention time of about 20 minutes increases in product purity leveled off. Increasing the retention time over about 20 minutes resulted in little additional purification at the expense of additional time. Thus, under the conditions employed in Example 4, the most preferred retention time is about 20 minutes.

The preferred capacity factor corresponding to a retention time of about 20 minutes as set forth in Example 4, can be used to calculate the preferred retention time on other columns. This determination can be made using either relationship (1) or (2):

$$k'=(t_r-t_o)/t_o \qquad (1):$$

$$t_r=(k')(t_o)+(t_o) \qquad (2):$$

In relationships (1) and (2), $t_r$ is the band retention time and $t_o$ is the column dead time. The column dead time can be determined in various ways known to those skilled in the art, such as by measuring the retention time of a compound which is not retained by the column. For a given set of column factors and constant separation conditions the column dead time is constant but the retention time varies for different compounds (oligomers).

The conditions used which resulted in about a 20 minute or greater retention time for TP-579 in Example 4, were found to correspond to a capacity factor greater than 5. At a retention time of about 20 minutes, the capacity factor was between 5 and 10. These results can be used to determine suitable conditions for the minimum preferred retention time (corresponding to a capacity factor of at least 5) and most preferred retention time (corresponding to a capacity factor of between 5 and 10) for other columns.

Optimal purification can be obtained on a particular column by adjusting one or more separation conditions such that the retention time corresponds to a k' greater than 5, preferably between 5 and 10. For a given column, $t_o$ is first determined, k' then is chosen to be greater than 5, preferably between 5 and 10, and relationship (2) is used to determine the optimal $t_r$. The optimal $t_r$ is achieved by varying the separation conditions such as pH, mobile phase composition, and temperature.

Effects of pH

As discussed above, lowering the pH of the mobile phase from about pH 7 to about pH 4 affects oligomer retention on silica by increased protonation of silanol groups. Chromatographic separation of neutral oligomers is preferably carried out within a pH range that insures oligomer stability, e.g., a pH of about 5 to 8, preferably at pH 6.0. For ionic oligomers which are weakly retained by silica, the preferred pH is about 4. For mixed ionic-neutral oligomers the preferred pH is between 4 and 6, depending upon the percentage of ionic linkages.

A pH less than about 4 is not preferred because of increased protonation of nucleoside amino groups at the lower pH which causes a decrease in retention time. Overall, the pH should be chosen to help give a capacity factor between 5 and 10, and should take into account the effect of pH on solubility and stability of the oligomers.

Varying the pH of the mobile phase allows one to have control over the retention time of an oligomer that would otherwise be weakly or strongly retained. However, it is important to consider the effect of changes in pH on oligomer stability and solubility. Where stability is affected by changes in pH, a preferred retention time is preferably obtained by appropriate selection of other conditions.

Temperature

As temperature increases, the solubility of oligomers in solution increases and the retention time decreases. Higher temperatures are believed to decrease the stability of the hydrogen bonding between the nucleoside amino group and the silica silanol group hydrogen. The temperature for the separation of neutral oligomers is preferably between 30°–70° C., more preferably at about 50° C. For ionic and mixed-ionic oligomers, a lower temperature will generally be employed to compensate for weaker retention of the silica column. Overall, the temperature should be chosen to help achieve a capacity factor between 5 to 10.

Mobile phase

Both the ion concentration of the aqueous buffer and percentage of organic solvent to water of the mobile phase affects retention. As the ion concentration of the aqueous buffer increases, retention time of all-methylphosphonates decreases while retention of oligomers with one or more diester or phosphorothioate increases. For methylphosphonates, the ion concentration of the aqueous buffer in the mobile phase affects retention by preventing the formation of hydrogen bonds between silanol groups and adenine, cytosine, or guanine nucleoside amino groups. For ionic oligomers, lowering buffer ion concentration is believed to decrease retention because of charge repulsion between negatively charged silanol groups and ionic groups. The ion concentration is preferably 2–100 mM ammonium acetate.

The percentage of organic solvent to water in the mobile phase affects retention; when the mobile phase is greater than about 40% organic solvent, retention is affected due to an oligomer's preference for the mobile phase or stationary phase. The stronger an oligomer's preference for the stationary phase, the more the oligomer will interact with the silica and the stronger the retention will be. The lower the percentage of organic solvent in the mobile phase, above the 40% then, the more an oligomer prefers the mobile phase and the weaker the retention will be.

Acetonitrile is preferred as the organic solvent for the mobile phase to separate oligomers (e.g., 30–70% acetonitrile). Superior purification was obtained using acetonitrile in the mobile phase in comparison to mobile phases with methanol or isopropanol.

Establishing And Predicting Retention Time

Establishing or predicting the retention time of oligomers facilitates the purification of oligomers. Two uses of establishing or predicting the retention time are: (1) determining which conditions can be used to obtain a k' for a fully synthesized oligomer to be between 5 and 10; and (2) establishing the retention time of a fully synthesized oligomer and predicting the retention time of its corresponding sequence failure. The later use is particularly beneficial in the purification of oligomers containing ionic linkages where the fully synthesized oligomer may be retained less than a sequence failure.

Establishing or predicting a retention time is achieved by first selecting a reference condition with a particular set of column factors and separation conditions. In a second step, relationships describing the effect on retention time of changing different separation conditions are empirically derived by measuring the retention time of a test oligomer under different conditions. In a third step, the derived relationships are used to either predict or establish a retention time of different oligomers under different conditions.

Such a reference condition suitable for methylphosphonate oligomers, diester oligomers and oligomers having both diester and methylphosphonate linkages is comprised of the following: a 25×0.46 cm Nucleosil silica column, a mobile phase of 50% acetonitrile/aqueous buffer, the aqueous buffer having an ion concentration of 2.0 mM ammonium acetate and a pH of 6.0, a temperature of 50° C., and a flow rate of 1 mL/min (hereinafter "reference condition 1"). The sample size should be less than 0.5 mg/mL of column volume.

The capacity factor for reference condition 1 is affected by changes in separation conditions, oligomer nucleoside composition, and the column factors as described by the relationships below:

$$\log k' = A + \Sigma R_{i(50)} \qquad (3):$$

In relationship (3), k' is the capacity factor for reference condition 1, "A" is a constant characteristic for a particular column, and $\Sigma R_i$ is the sum of interaction energies between individual nucleosides present in the oligomer, diester groups, and the silica surface. Except for thymine and uracil, each nucleoside in the oligomer contributes some faction $R_i$ to the total interaction energy.

The total interaction energy may be calculated by relationship (4):

$$\Sigma R_{i(50)} = 0.090\, g + 0.155\, a + 0.140\, c - 1.00\, d \quad (4)$$

In relationship (4) "g" refers to guanine, "a" refers to adenine, "c" refers to cytosine and "d" refers to diester groups.

As noted above, the retention time $t_r$ and k' are elated by relationships (1) and (2):

$$k' = (t_r - t_o)/t_o \quad (1)$$

$$t_r = (k')(t_o) + (t_o) \quad (2)$$

The column dead-time to can be experimentally determined or calculated using the following relationship:

$$t_o = V_m/F \quad (5)$$

In relationship (5) "F" is the flow rate and $V_m$ is the column dead-volume.

The column dead-volume will be different for an oligomer containing a diester group and an all-methylphosphonate ("all-MP") oligomer. This difference is due the negatively charged diester group being repelled by the charged silanol groups in the particle pores.

$$(\text{all-MP})\ V_m = (0.5)(L)(d_c^2) \quad (6)$$

$$(5'\text{-diester})\ V_m = (0.36)(L)(d_c^2) \quad (7)$$

In the above relationships "L" is the column length in cm and $d_c$ is the column internal diameter in cm.

The column constant "A" for relationship (3) can be calculated for a given column by measuring the retention time of a test oligomer having a known nucleoside composition in the following manner:

A) Determine $\Sigma R_{i(50)}$ of the test oligomer using relationship (4).

B) Measure the retention time of the test oligomer using reference condition 1.

C) Determine $V_m$ using either relationship (6) or (7) (if a diester group is present relationship (7) is used).

D) Determine $t_o$ using relationship (5), $V_m$ determined in step (C), and the known flow rate.

E) Determine the capacity factor using relationship (1), $t_r$ determined in step (B), and $t_o$ determined in step (D).

F) Determine "A" using relationship (3), k' determined in step (E) and $\Sigma R_{i(50)}$ determined in step (A).

Once "A" is determined for a given column using a test oligomer and reference condition 1, the retention time and k' for other oligomers can be established or predicted, based on empirically derived relationships. Relationships have been derived describing the effect of temperature, ion concentration, percentage of acetonitrile and oligomer structure.

The following relationships have been found to describe the effect of changing the percentage of acetonitrile in the mobile phase from that used in reference condition 1.

$$\Sigma R_i = [\Sigma R_{i(50)}][f(\% B)] \quad (8)$$

In relationship (8), % B refers to mobile phase composition of acetonitrile/aqueous buffer, $\Sigma R_{i(50)}$ refers to the value of interaction energies under reference condition 1 as determined in relationship (4), and "f" is a function of % B as described in relationships (9) and (10). Experimental data have been collected for 30–60% B and used to numerically define f(% B) as a function of % B. This relationship has been extrapolated to higher values of % B. Based upon this approach f(% B) can be expressed by the following relationships:

$$(\text{for }\% B > 61\%)\ f(\% B) = 10^{0.018(\% B - 50)} \quad (9)$$

$$(\text{for }\% B < 61\%)\ f(\% B) = 2.9 - 0.113(\% B) + 0.0015\,(\% B)^2 \quad (10)$$

The effect of changing mobile phase composition can e determined in the following way:

A) Determine f(% B) using either relationship (9) or (10).

B) Determine $\Sigma R_{i(50)}$ from the known oligomer composition and relationships (4).

C) Determine $\Sigma R_i$ using relationship (8), $\Sigma R_{i(50)}$ determined in step (B), and f(% B) determined in step (A).

D) Determine the capacity factor using relationship (3), "A" derived for the column used, and $\Sigma R_i$ determined in step (C).

E) Determine retention time using relationship (2).

Using the above procedure, the effect of a change in mobile phase composition can be determined. Thus, a mobile phase having a particular organic solvent/aqueous buffer composition can be chosen to achieve a desired retention time.

The retention time can also be altered by changing the buffer concentration. The effect of buffer concentration on oligomer retention is somewhat complex and not fully defined for all oligomers and conditions. An approximate relationship has been empirically derived from a limited data set and is described in relationship $$\log k_{50} = -0.64 + [\Sigma R_{i(50)}][f(\% B)] - d - 0.00021(g+a+c)(C-2) + 0.14d \log(C)(0.01) - 0.105d \quad (11)$$

In relationship (11) $k_{50}$ is the k' at 50° C., "C" is the buffer ion concentration in mM. If "C" used is greater than 50 mM, "C" in relationship (11) is set equal to 50. The other terms are as described above. Buffer ion concentration greater than 50 mM has little further effect on retention of an oligomer containing a 5'-diester or phosphodiester linkage.

Using relationship (11), the effect of ion concentration on capacity factor can be determined. Thus, the ion concentration can be adjusted to help establish a desired k' or retention time for different oligomers. In addition, relationship (11) may be used to predict the retention time of oligomers at various ion concentrations. We have found that predictions using relationship (11) are less reliable for mixed diester-methylphosphonate oligomers than all-methylphosphonate oligomer.

The retention time and capacity factor can also be altered by varying the temperature. The effect of temperature is given by the following relationships:

$$\log k' = (\log k_{50}) - B[(1/273) - 1/T)] \quad (12)$$

$$B = (950 \log k_{50}) + 540 \quad (13)$$

In relationships (12) and (13), T is the temperature in ° K. (273+temperature in ° C.), k' refers to the value of k' at the new temperature, and log $k_{50}$ refers to log of the capacity factor at 50° C.

Relationship (12) may be used to determine the effect of temperature on capacity factor by first determining "B" from equation (13) and the log $k_{50}$ from relationship (3). Relationship (12) may used to determine k' at different temperature. Thus, the effect of temperature can be calculated and the desired temperature chosen.

To assist in understanding the present invention, the following examples are included which describe the results of series of experiments. The following examples, and those previously disclosed in this specification, relating to this invention should not be construed as specifically limiting the invention and such variation of the invention, now known or later developed, which would be within the purview of one skilled in the art are considered to fall within the scope of the present invention as hereinafter claimed.

EXAMPLES

Synthesis

Example 1

Comparison to Separation Using Normal Phase Chromatography Silica To Reverse-Phase Chromatography The use of silica for the purification of impure (up to 30% purity) all-methylphosphonate oligomer provides a better purification than reverse phase chromatography. The all-methylphosphonate oligomer TP-579 (TGG-CCA-TGG-CAG-CTG) [SEQ. ID. NO. 5] was separated using a silica column and a reverse phase column. A sample weight of 0.01 gm were added to the columns. Column (A), the reverse-phase column, was a Whatman C18 column (25×0.46 cm) used under the following conditions; 10–25% acetonitrile/water gradient in 15 minutes, 1.0 mL/min, at 30° C. Column (B), the normal phase silica column, was a Kromasil silica column (25×0.46 cm) used under the following conditions; 50% v/v acetonitrile/buffer (pH 6.0, 50 mM potassium acetate), 1.0 mL/min, at 50° C.

Figure 1B:
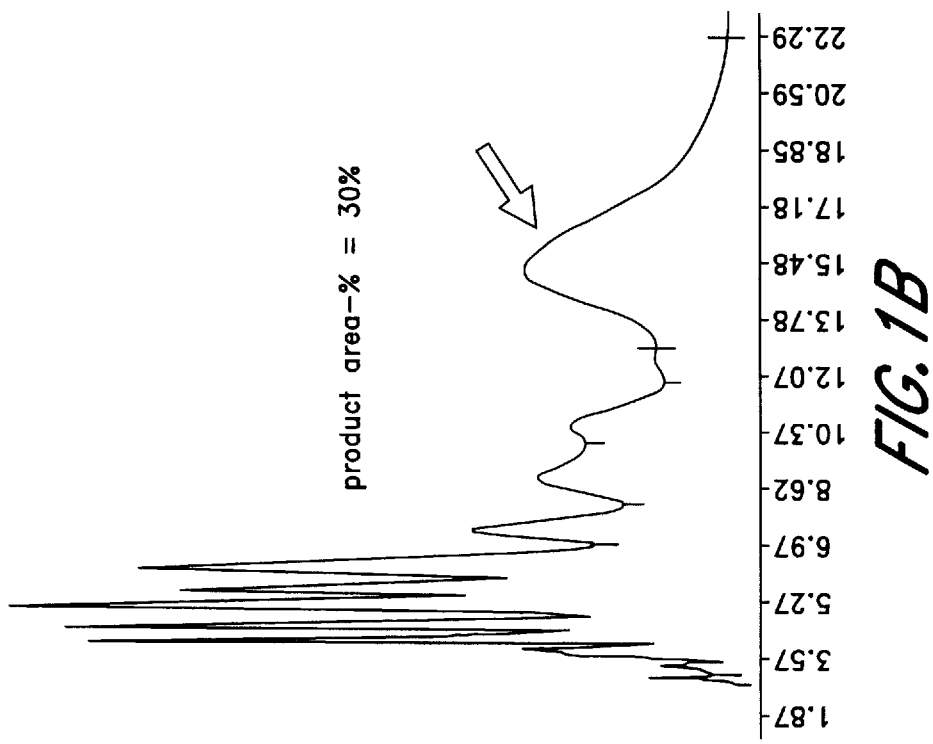
Figure 3B:
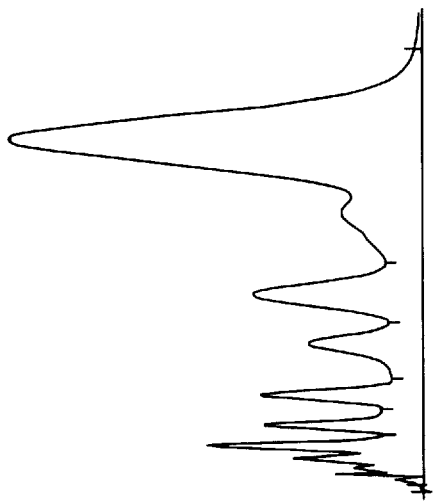
FIGS. 3A to 3D, depict the preparative separation of an all-methylphosphonate oligomer, 1366-3, on a Kromasil column at different sample amounts: 0.1 mg (3A), 2 mg (3B), 5 mg (3C) and 10 mg (3D).
Figure 3D:
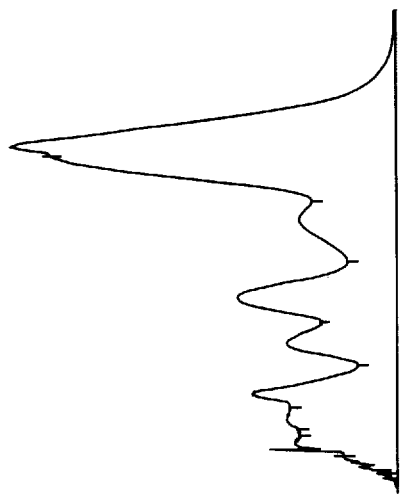
Figure 3A:
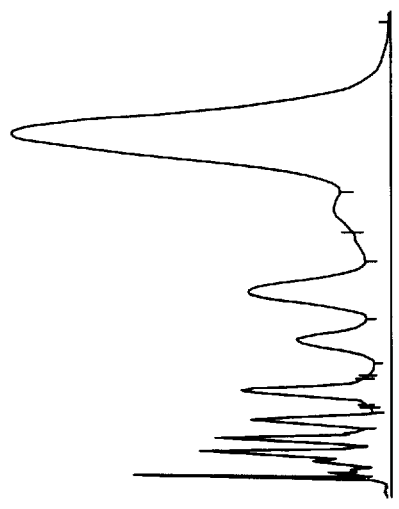
Figure 3C:
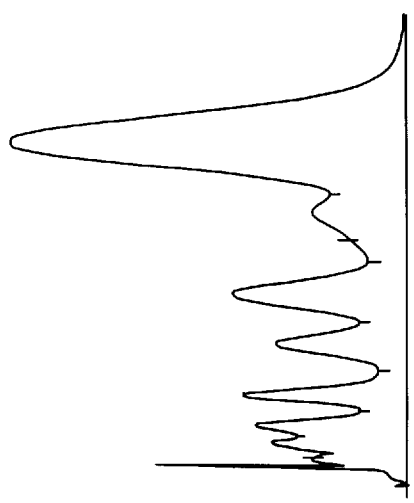

As seen in FIGS. 1A and 1B, the large product peak (arrow) eluted at the end of the chromatogram and various impurity bands eluted prior to this band. The fractional product area for column (A) (FIG. 1A) was 65%. In contrast, the fractional product area for column (B) (FIG. 1B) was 30%. The silica column as indicated by the smaller fractional product area gave a superior purification than the C18 column.

Example 2

Separation on Different Silica Columns

The all-methylphosphonate oligomer TP-579 [SEQ. ID. NO. 5] was separated on four different silica columns: (A) Kromasil, (B) Cyclobond (β-cyclodextrin), (C) glucose-silica, and (D) diol-silica. The separation conditions were the same except for the temperature. The Kromasil column was run at 50° C., while the other columns were run at 30° C. All of the columns were 25×0.46 cm, and used a buffer of 2 mM ammonium acetate (pH 6.0), with a flow rate of 1.0 mL/min. Other conditions were as shown in Table 1.

TABLE 1

| Column | %-acetonitrile | temperature (°C.) |
|---|---|---|
| silica | 50 | 50 |
| Cyclobond | 60 | 30 |
| glucose | 70 | 30 |
| diol | 71 | 30 |

As seen in FIGS. 2A to 2D, equivalent separation was observed on the bare silica (Kromasil) FIG. 2A and the hydrophilic silica colums (cyclobond (FIG. 2B), glucose silica (FIG. 2C) and diol-silica (FIG. 2D)).

Example 3

Preparative Separation on Kromasil

Different amounts of the all-methylphosphonate oligomer 1366-3 (5'-GTCTTTGAACTCTGCTTA-3') [SEQ. ID. NO. 6] were purified on a silica column. Kromasil columns (25×0.46 cm) were used under the following conditions; 50% v/v acetonitrile/buffer (pH 6.0, 50 mM potassium acetate), a flow rate of 1.0 mL/min, and a temperature of 50° C. The sample size of 1366-3 loaded onto the columns were (A) 0.1 mg, (B) 2 mg, (C) 5 mg, and (D) 10 mg. As seen in FIGS. 3A to 3D and Table 2, increasing the sample size up to 10 mg did not affect the purification.

TABLE 2

| Weight | Recovery = product % | FIG. No. |
|---|---|---|
| 0.1 mg | 56% | 3A |
| 2 mg | 53 | 3B |
| 5 mg | 52 | 3C |
| 10 mg | 50 | 3D |

Example 4

Determination Of Preferred Capacity Factor (k')

Figure 4:
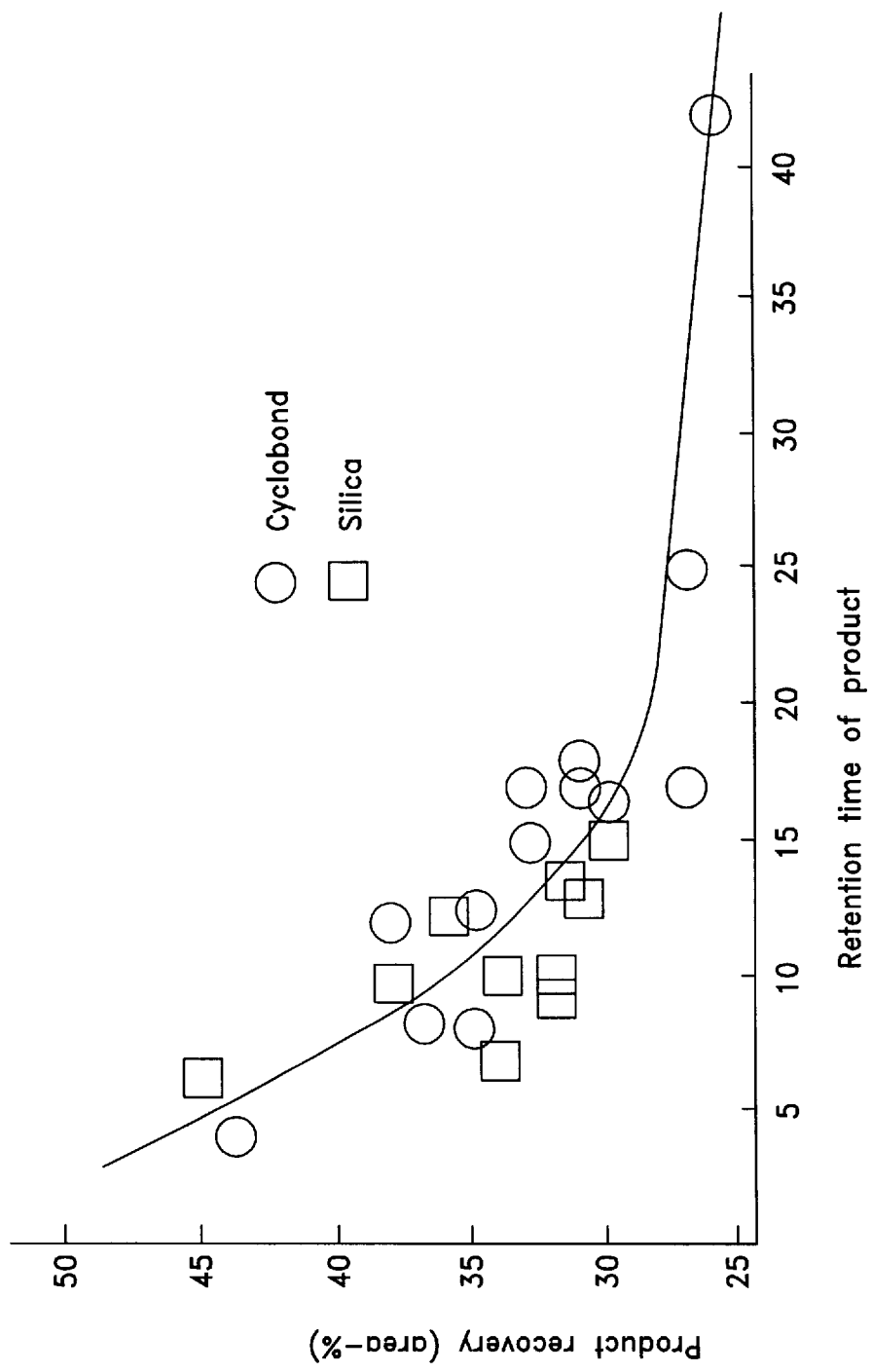
FIG. 4, depicts a graphical summary of purity of product as a function of the retention time. The all-methylphosphonate oligomer, TP-579, was separated from various impurities using either a Kromasil column (squares) or a cyclodextrin-bonded column (circles). Column conditions for the silica column were 50° C., 1.0 ml/minute and for the cyclodextrin column were 30° C., 1.0 ml/minute.

The optimal capacity factory was determined using P-579 [SEQ. ID. NO. 5]. TP-579 has the nucleoside sequence of TGG-CCA-TGG-CAG-CTG. Purification was performed using either a Kromasil column (25×0.46 cm) (FIG. 4, squares) or a cyclodextrin-bonded column (25×0.46 cm) (FIG. 4, circles). A 0.1 mg sample having a purity of 27% was loaded onto the column. The Kromasil column was run at a temperature of 50° C. and a flow rate of 1.0 mL/min. The cyclodextrin column was run at a temperature 30° C. and a flow rate of 1.0 mL/min. Different retention times were obtained by varying the aqueous buffer composition, the pH, and the percentage of acetonitrile. When the retention time was about 20 minutes near maximum purity was obtained.

Example 5

Retention Time As A Function Of Structure

Figure 5:
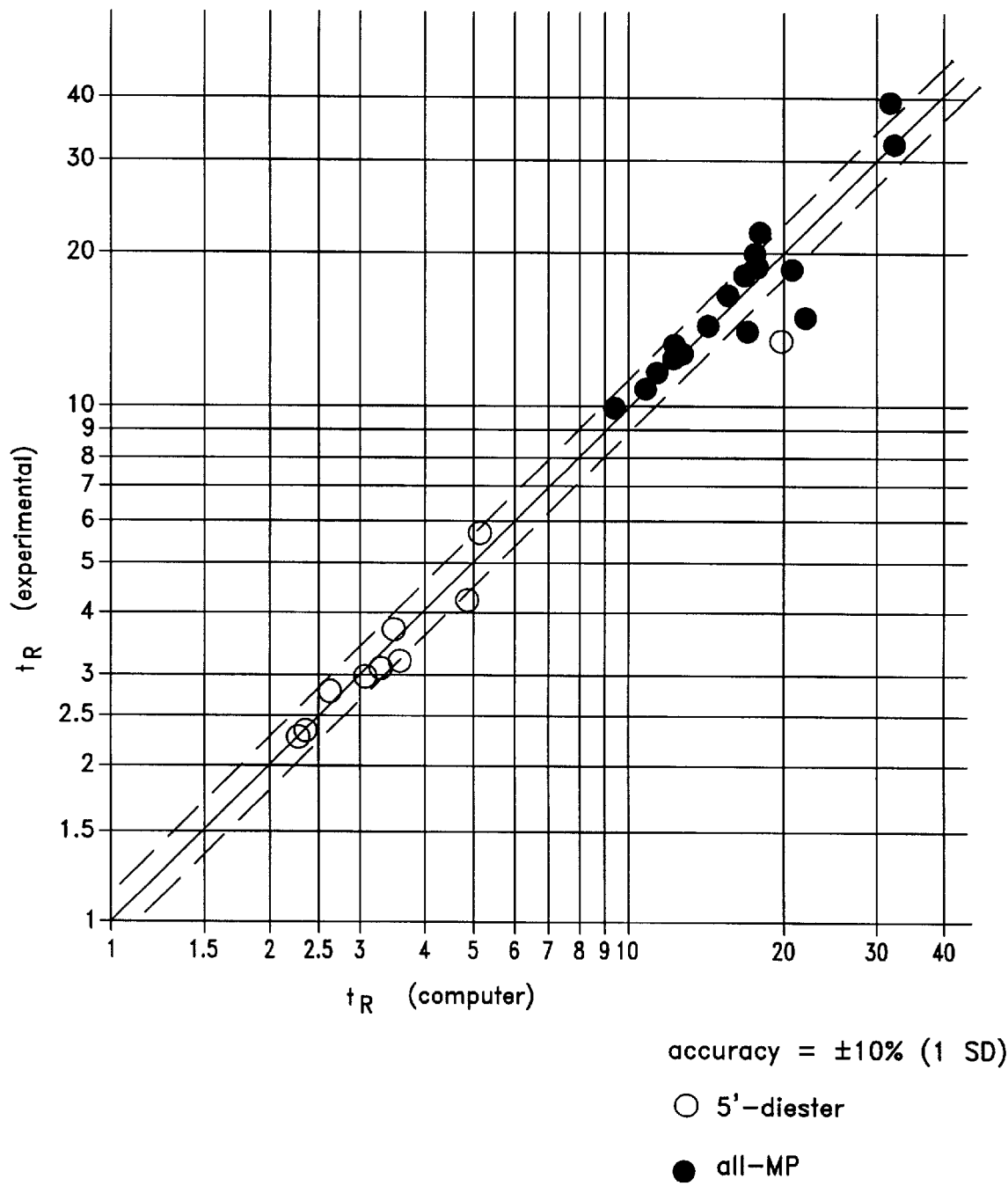
FIG. 5, depicts a graph showing the accuracy of predicting the retention time of different all-methylphosphonate oligomers and 5'-diester-methylphosphonate oligomers as a function of oligomer composition using a (25×0.46 cm) nucleosil silica column, eluting with 50% ACN buffer (2 mM NH$_4$Ac, pH 6.0). Open circles refer to 5'-diester-methylphosphonate oligomers. Closed circles refer to all methyl phosphonate oligomers ("all-MP").

The actual retention time of different 5'-diester-methylphosphonate oligomers and all-methylphosphonate oligomers were compared to the retention time predicted as described in the specifications above. FIG. 5, shows the comparison of actual retention time versus predicted retention time. Different 5'-diester-methylphosphonate oligomers (FIG. 5, open circles) and all-methylphosphonate oligomers (FIG. 5, closed circles) were separated on a Nucleosil silica column (25×0.46 cm) using the following conditions: 50% acetonitrile/aqueous buffer; aqueous buffer is 2 mM ammonium acetate at a pH of 6.0, a temperature of 50° C., and a flow rate of 1 mL/min. The solid straight line corresponds to exact agreement between the predicted and experimental retention times.

Example 6

Acetonitrile Percentage

Figure 6:
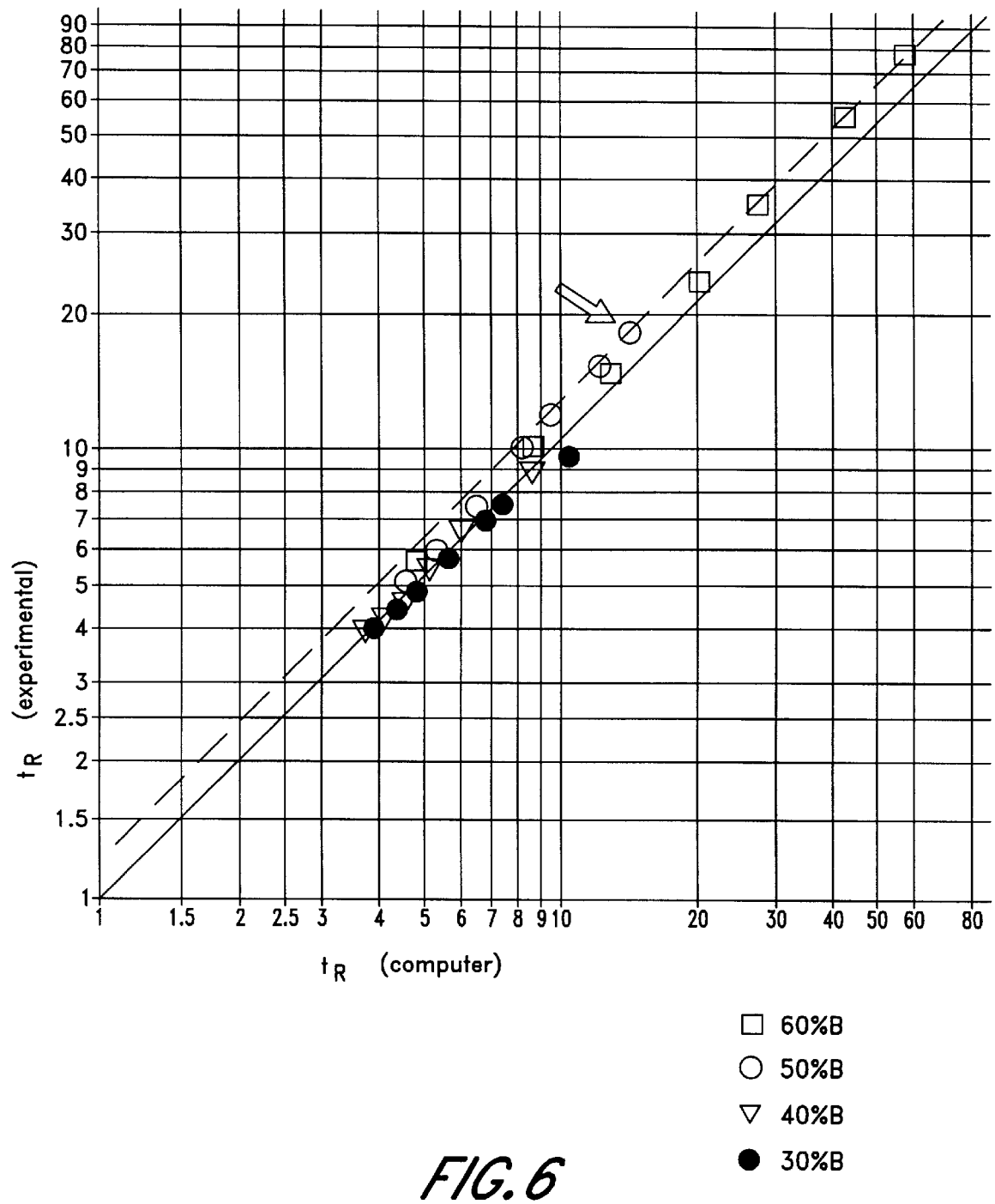
FIG. 6, depicts a graph showing the accuracy of predicting the retention time of the all-methylphosphonate oligomer 1366-3 as the acetonitrile percentage is changed percentages of acetonitrile (% B) were 60% (open box), 50% (open circle), 40% (open trangle) and 30% (closed circle). Other column conditions are as for FIG. 2.

The retention time of the all-methylphosphonate oligomer 1366-3 [SEQ. ID. NO. 6] and its sequence failure contaminants using different acetonitrile percentages were determined experimentally and predicted as described above in the specification. The results are shown in FIG. 6. Separation was performed using Nucleosil silica columns (25×0.46 cm) under the following conditions: an aqueous buffer of 2 mM ammonium acetate at a pH of 6.0; a temperature of 50° C.; a flow rate of 1 mL/min; and percentages of acetonitrile (% B) of 60% (FIG. 6, open box), 50% (FIG. 6, open circle), 40% (FIG. 6, open triangle), and 30% (FIG. 6, closed circle). The solid straight line corresponds to exact agreement between the predicted and experimental retention times.

Example 7

Temperature

Figure 7:
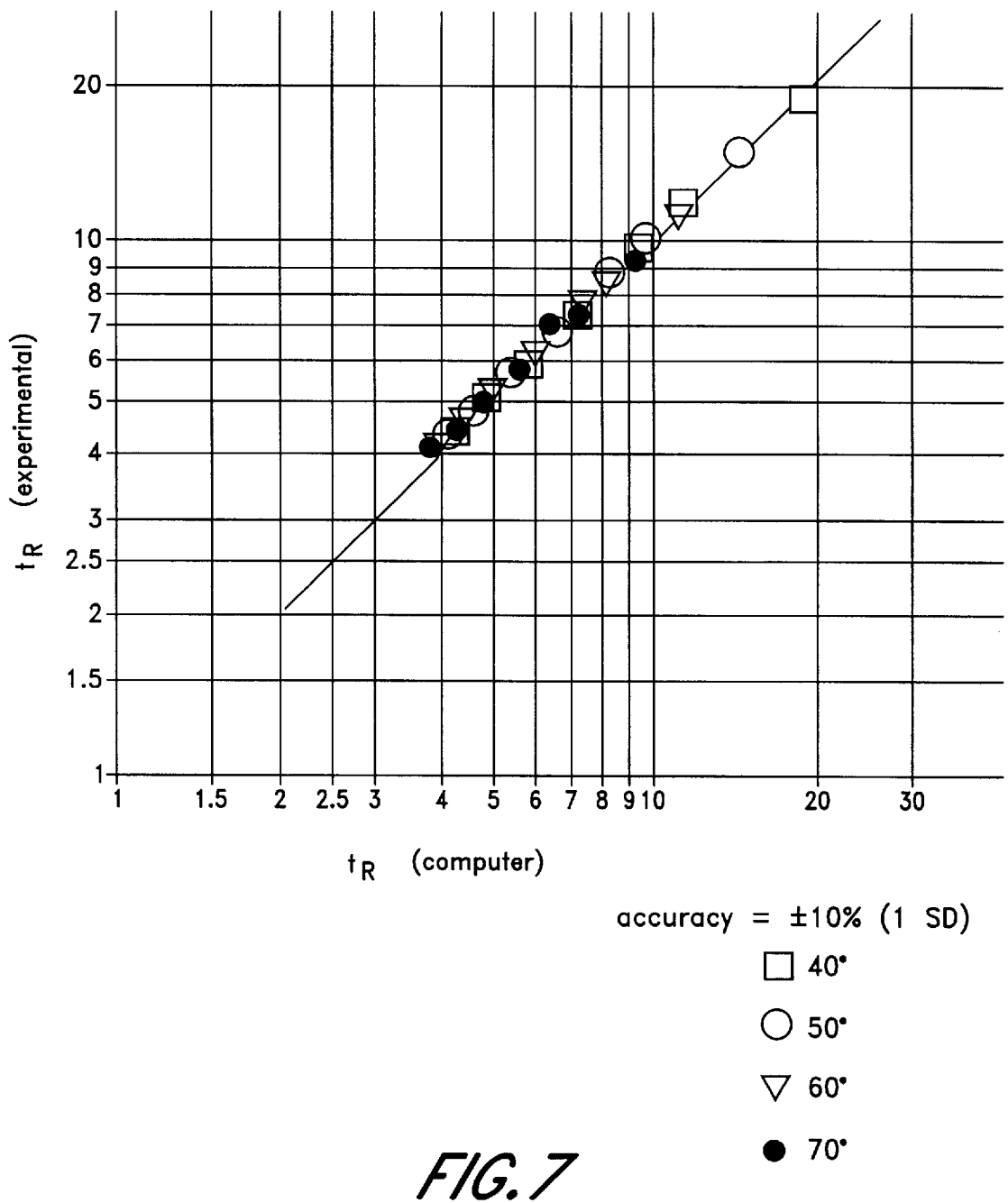
FIG. 7, depicts a graph showing the accuracy of predicting the retention time of the all-methylphosphonate oligomer 1366-3 as a function of temperature. Other column conditions are as for FIG. 2.

The retention time of the all-methylphosphonate oligomer 1366-3 [SEQ. ID. NO. 6] as a function of temperature was determined experimentally and predicted as described above in the specification. Separations were achieved on Nucleosil silica columns (25×0.46 cm) under the following conditions: 50% acetonitrile/aqueous buffer; aqueous buffer is 2 mM ammonium acetate at a pH of 6.0; a flow rate of 1 mL/min; and temperatures of 40° C. (FIG. 7, open squares), 50° C. (FIG. 7, open circles), 60° C. (FIG. 7, open upside down triangle) and 70° C. (FIG. 7, closed circle). The solid straight line corresponds to exact agreement between the predicted and experimental retention times. The overall accuracy of predicted retention time was about 10%.

Example 8

Purification Of All-Phosphorothioate Oligomer

Figure 8:
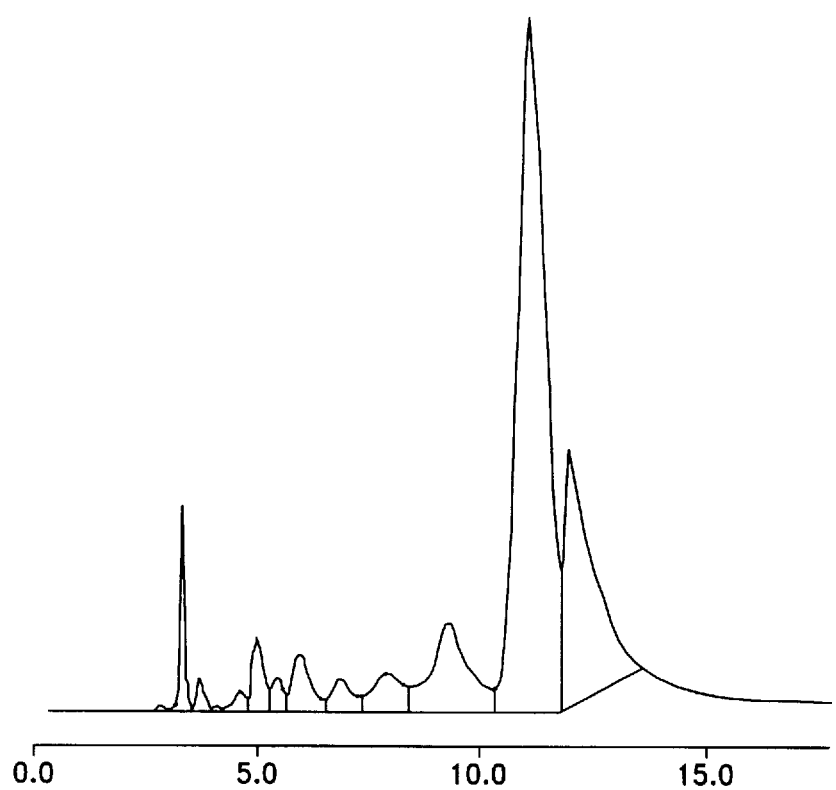
FIG. 8, depicts a chromatogram showing the purification of an all-phosphorothioate oligomer on silica run isocratically at pH 4.0.

The isocratic purification of an all-phosphorothioate oligomer, 1679 (5'-GCTTTTGAACTCTGCTTA-3') [SEQ. ID. NO. 7] is shown is FIG. 8. The following separation conditions were used: Kromasil column (25×0.46 cm): 200 mM ammonium acetate, 13% cetonitrile, a flow rate of 1 mL/min, a pH of 4.0, at room temperature. As seen in FIG. 8, silica chromatography was able to separate an all-phosphorothioate oligomer from various impurities.

Example 9

Separation Of Oligomers Having 2'-O-methyl Pyrimidine Nucleosides

This example describes the separation of three different 5'-diester-methylphosphonate oligomers having 2'-O-methyl pyrimidine nucleosides and 2'-deoxypurine nucleosides using silica. The following oligomers were used:

Genta #1 5'-CpAU-GAC-CGC-ACC-ACG-CUC-3' [SEQ. ID. NO. 8]

Genta #2 5'-UpUC-CUC-CUG-CGG-3' [SEQ. ID. NO. 9]

Genta #3 5'-CpUC-UCU-CUC-UCU-CUC-T-3' [SEQ. ID. NO. 10]

The separation of the three oligomers were studied as a function of mobile phase and temperature. Mobile phase composition was varied from 40% to 70% acetonitrile, and temperature was varied from 30° C. to 60° C. Separations were performed on a (25×0.46 cm), Nucleosil silica 10-μm, with an aqueous buffer of 50 mM ammonium acetate buffer (pH 6.00), and a flow rate of 1 mL/min. When acetonitrile percentage (% B) was varied the temperature was constant at 50° C. When temperature (Table 3 "tempt") was varied the acetonitrile percentage was keep constant at 50%. Table 3 shows overall average values of experimental ("expt") retention time and calculated retention time ("calc") as a function of acetonitrile composition and temperature.

TABLE 3

| | Retention time (min) | |
|---|---|---|
| | Expt. | Calc. |
| Condition % B | | |
| 40% | 4.7 | 3.6 |
| 50% | 8.0 | 6.5 |
| 60% | 7.0 | 5.9 |
| 70% | 33.2 | 32.1 |
| Tempt. | | |
| 30° C. | 9.8 | 7.9 |
| 45° C. | 7.5 | 6.3 |
| 50° C. | 7.1 | 5.8 |
| 60° C. | 6.0 | 5.2 |

The average deviation in minutes shown in Table 1 is 1.3. These results indicate that 2'-O-methyl ribose-based methylphosphonate oligomer derivatives are separated in an analogous manner as deoxyribose based methylphosphonate oligomer derivatives. Thus, the models used to separate deoxyribose based methylphosphonate derivatives apply to ribose based methylphosphonate oligomer derivatives.

Example 10

Comparison Of ODS Reversed-Phase and HILIC Normal-Phase Columns With An 18-mer Methylphosphonate Oligonucleotide Containing a Single 5'-Terminal Phosphodiester A sample of the following methylphosphonate oligomer was evaluated according to this example:

5'-GpTCTTCCTGCCCCATTGC-3' [SEQ. ID. NO. 11]

The underlined letters indicate bases which are joined by methylphosphonate linkages and 'p' indicates a phosphodiester linkage. This sample was deprotected using a brief treatment with concentrated aqueous ammonium hydroxide and a six hour treatment with 1:1 ethylenediamine/95% ethanol. It was then purified by preparative scale reverse phase HPLC using a Hamilton PRP-1 column (4.1 mm i.d.×250 mm long).

HPLC analyses were performed with a Beckman System Gold™ apparatus equipped with a Model 168 Diode-Array UV detector. Samples (typically 100 milli-$A_{260}$ units) were prepared in 50% acetonitrile-water and were injected in 20 μL aliquots using a 100 μL sample loop. Peaks were monitored and recorded at 260 nm. Conditions for "reverse phase" and "normal-phase" chromatography were as follows. Reversed-phase: Whatman ODS-3 RAC II column (4.6 mm i.d.×100 mm long); Buffer A=50 mM triethylammonium acetate (TEAA, pH 7); Buffer B=50% acetonitrile in 50 mM TEAA (pH 7); linear gadient of 0–60% Buffer B over 30 minutes at a flow rate of 1.0 mL/min. Normal phase: Poly LC polyhydroxyethyl A (HILIC) column (4.6 mm i.d.×250 cm long); Buffer A=50 mM triethyammonium acetate (TEAA, pH 7); Buffer B=acetonitrile; linear gradient from 90–30% Buffer B over 20 minutes at a flow rate of 1 mL/min.

The conditions described above for reverse-phase analysis gave a single peak (retention time=25.88 min.), which was expected since this sample had been purified by preparative reverse-phase HPLC. However, the conditions for normal-phase HPLC using the HILIC column showed this sample to contain at least four contaminants appearing at later retention times (main peak=12.61 min.; contaminants= 12.78 min., 14.25 min., 15.19 min. and 16.48 min.).

Example 11

Fractionation of an 18-mer Methylphosphonate Oligonucleotide Containing a Single 5'-terminal Phosphodiester Linkage BY Normal-phase HPLC and Analysis of Fractions By Polyacrylamide Gel Electrophoresis.

A sample of the oligomer [SEQ. ID. NO. 11] described in the preceeding example (50 µg) was fractionated by normal-phase HPLC using the conditions described above. The main peak and four contaminant peaks were designated as peaks 1–5, respectively. Each of the peaks was collected separately and lyophilized to remove buffer salts. Next, samples from each peak were labelled with $^{32}$P according to the following protocol. To a 1.5 ml polypropylene microfuge tube were added 1 µL of each peak ($A_{260}$=1 in 50% acetonitrile/water), 1 µL of 10× polynucleotide kinase buffer (US Biochemicals, Inc.), 1 µL of [$\gamma$-$^{32}$P] ATP (10 µCi/µL, 3000 Ci/mmol), 7 µL of water, and 0.5 µL of T4-polynucleotide kinase (10 units, Stratagene, Inc.). The tubes were incubated at room temperature for 90 minutes and then diluted with 10 µL of a solution containing 90% formamide, 1×tris-borate-EDTA buffer (TBE buffer=89 mM tris-borate, 25 mM EDTA, pH 8.3), and 0.25% bromphenol blue dye. 1 µL aliquots from these reactions were then loaded onto a 20% polyacrylamide (19:1 acrylamide/bisacrylamide)/7M urea gel (0.5 mm thick×20 cm wide×30 cm long) containing 1× TBE. The gel was electrophoresed at 900 volts for 150 minutes using 1×TBE buffer in the upper and lower reservoirs. The wet gel was then removed, covered with plastic wrap and exposed to XAR-5 film (Eastman Kodak) for 15 minutes. The $^{32}$P-kinased samples corresponding to Peaks 2–5 gave single bands on the gel which migrated more slowly than the sample corresponding to Peak 1. Thus, Peaks 2–5 were shown to be distinct from Peak 1 by this procedure. One possible explanation for the slower migrating potentials of Peaks 2–5 is that they resulted from side-reactions with ethylenediamine. Such modifications would reduce the net negative charge of these oligomers, since ethylenediamine moieties can take a positive charge at pH values lower than about 9.

Examples 10 and 11 demonstrate that a sample of methylphosphonate oligomer appearing to be homogeneous by reverse phase HPLC in fact contained a number of impurities. These impurities were separated using the normal-phase procedure and were shown to be distinct from the main component by polyacrylamide gel-electrophoresis.

Example 12

Figure 9:
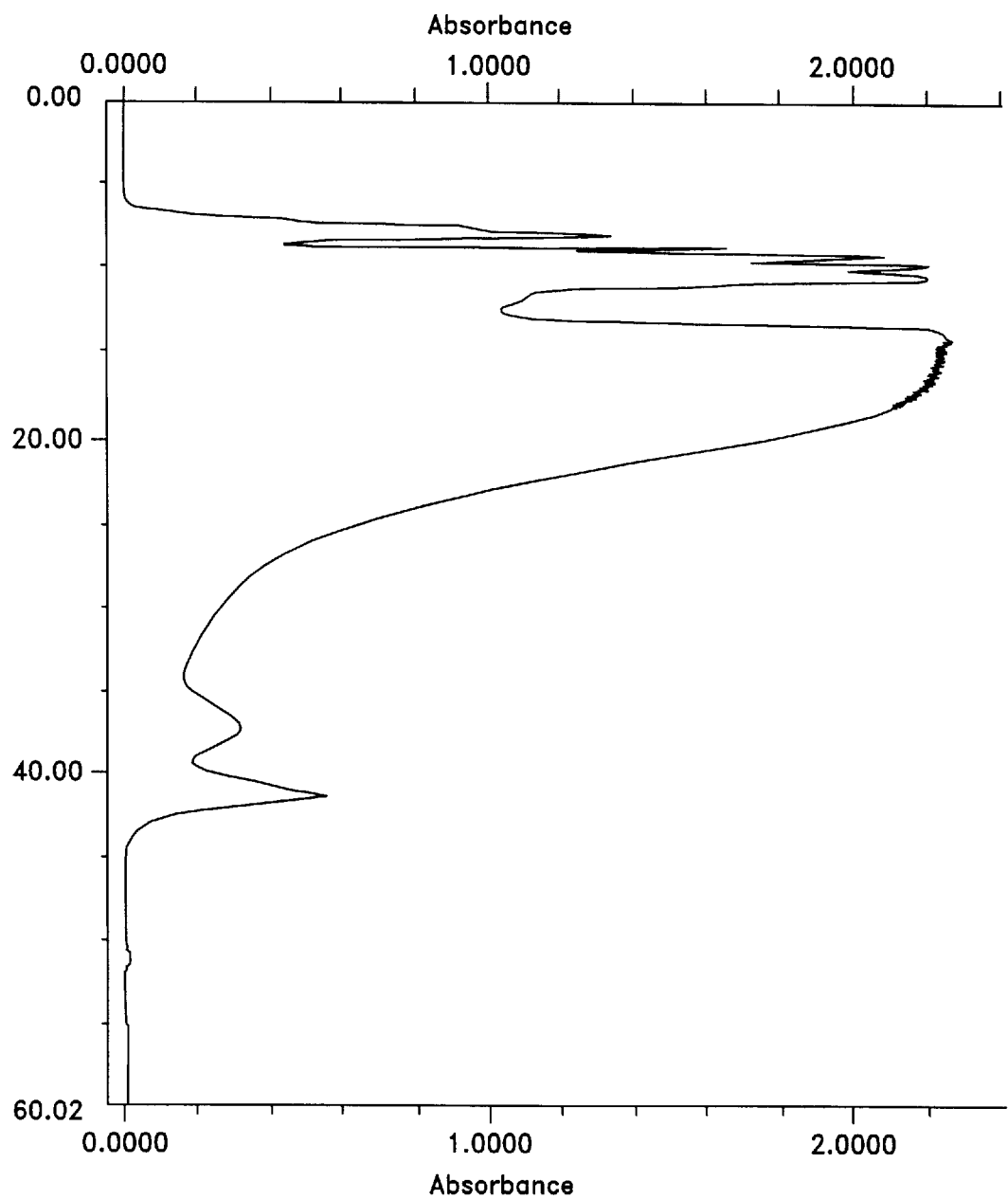
FIG. 9 depicts a chromatogram demonstrating purification of a 2'-O-methyl oligomer having an alternating Rp-methylphosphonate-diester backbone.

Purification of 2'-O-methyl Alternating Rp-methylphosphonate-diester Backbone Oligomers A 2'-O-methyl oligomer (GGUAUAUCCAGUGAUCUUCUUCTC) [SEQ. ID. NO. 12] containing alternating Rp-methylphosphonate and diester linkages was synthesizd in a stepwise manner using chirally pure methylphosphonate dimer synthons on a Pharmacia Oligopilot. After deprotection with ethylenediamine and subsequent neutralization and desalting, the oligomer was (about 483 O.D.s) was purified by normal phase chromatography on a 4.6 mm×250 mm cyclobond column (β-cyclodextrin derivatized, 5 µm, 60 Å pore, spherical silica) which had been equilibrated with the mobile phase (57% acetonitrile (ACN), 57% 100 mM ammonium acetate (NH4Ac), pH 5.0), at a flow rate of 1 ml/minute. Fractions eluting at 34 to 50 minutes and 51 to 60 minutes were pooled to give the product full-length oligomer. FIG. 9 depicts the chromatogram obtained.

Figure 10:
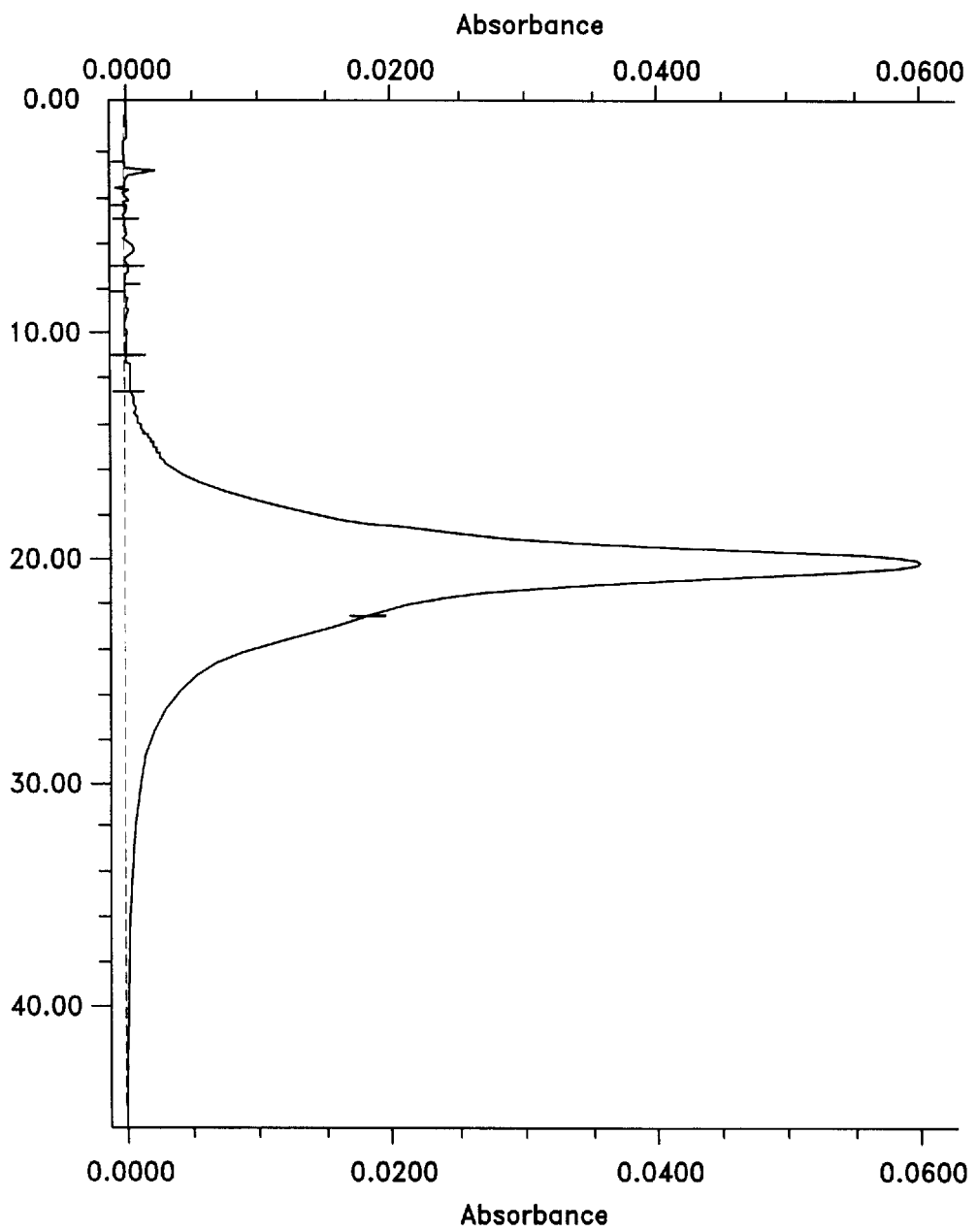
FIG. 10 depicts the confirmatory chromatogram for the oligomer of FIG. 9.

To confirm purification of the full-length oligomer, a small portion was injected on a 4.5 mm×250 mm cyclobond column (β-cyclodextrin derivatized, 5 µm, 60 Å pore, spherical silica; Astec, Inc.) which had been equilibrated with the mobile phase (55% ACN, 45% 100 mM NH$_4$Ac, pH 5.0. The method was run isocratically with the above conditions. The retention time of full length oligonucleotide was 20.5 min. FIG. 10 depicts the chromatogram obtained.

Example 13

Figure 11:
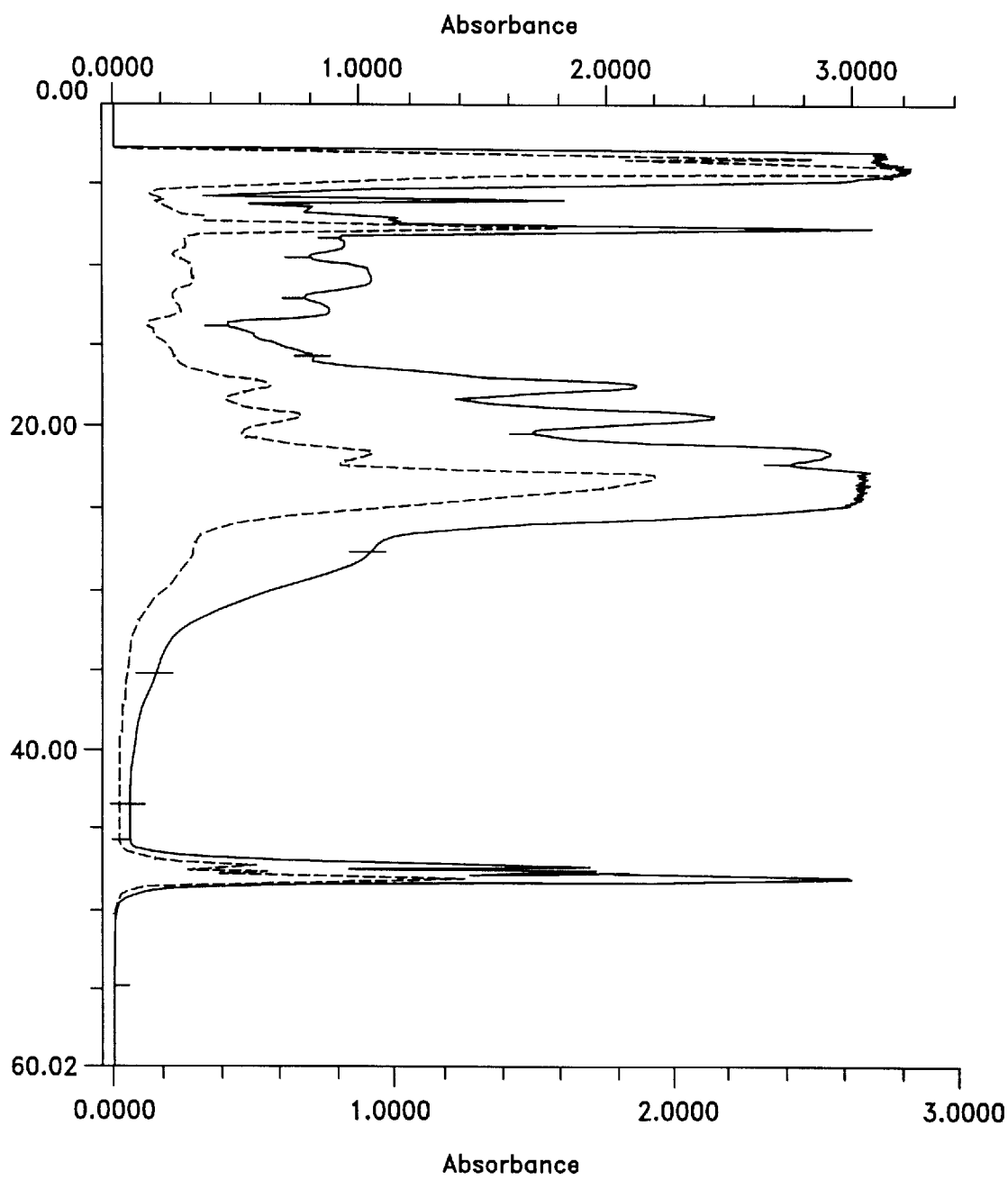
FIG. 11 depicts a chromatogram demonstrating purification of a 2'-deoxy oligomer having an alternating Rp-methylphosphonate-diester backbone with a phosphorothioate core.

Purification of 2'-Deoxy Alternating Rp-methylphosphonate-diester Backbone Oligonucleotides With A Phosphorothioate Core A 2'-deoxy oligomer [GCCG(GTACCT)GCTTGACAAG] [SEQ. ID. NO. 13] containing alternating Rp-methylphosphonate and diester linkages with a core of phosphorothioate linkages (indicated by the parentheses) was synthesized in a stepwise manner using chirally pure methylphosphonate dimer synthons and β-cyanoethyl amidite monomers on a Biosearch Expedite synthesizer. After deprotection with ethylenediamine and subsequent neutralization and desalting, the oligomer (about 341 O.Ds) was purified by normal phase chromatography on a 4.6 mm×250 mm cyclobond column (β-cyclodextrin derivatized, 5 µm, 60 Å pore, spherical silica) which had been equilibrated with the mobile phase (55% ACN, 45% 100 mM NH$_4$Ac, pH 6.0), at a flow rate of 1 ml/minute. Fractions eluting at 23 to 32 minutes were pooled to gie the product full length oligomer. FIG. 11 depicts the preparative chromatogram obtained.

Figure 12:
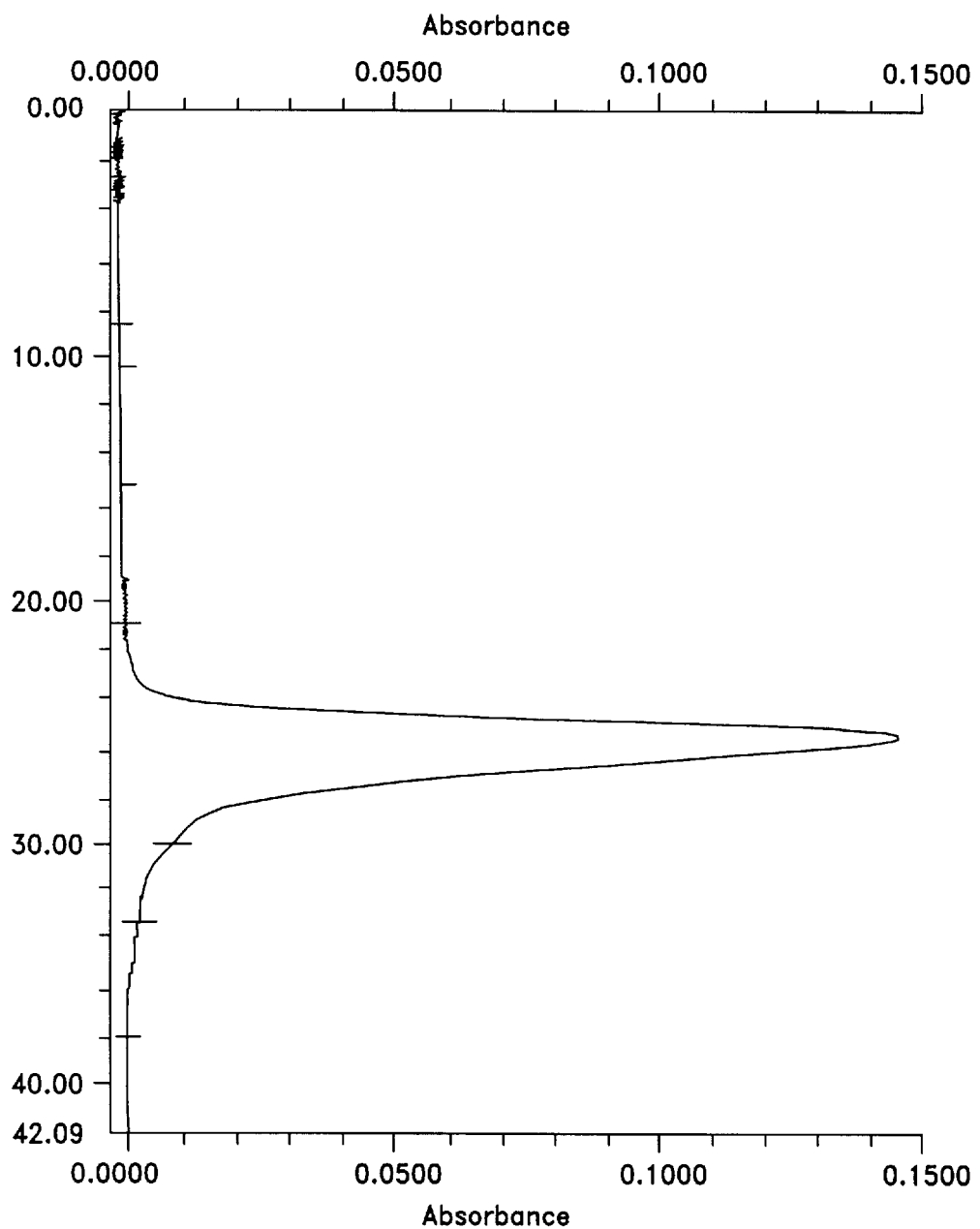
FIG. 12 depicts the confirmatory chromatogram for the oligomer of FIG. 11.

To confirm purification of the full length oligomer, a small portion was injected on a 4.5 mm×250 mm cyclobond column (β-cyclodextrin derivatized, 5 µm, 60 Å pore, spherical silica; Astec, Inc.) which had been equilibrated with the mobile phase (55% ACN, 45% 100 mM NH$_4$Ac, pH 6.0). The method was run isocratically with the above conditions. The retention time of full length oligonucleotide was 25.9 min. FIG. 12 depicts the chromatogram.

Example 14

Figure 13:
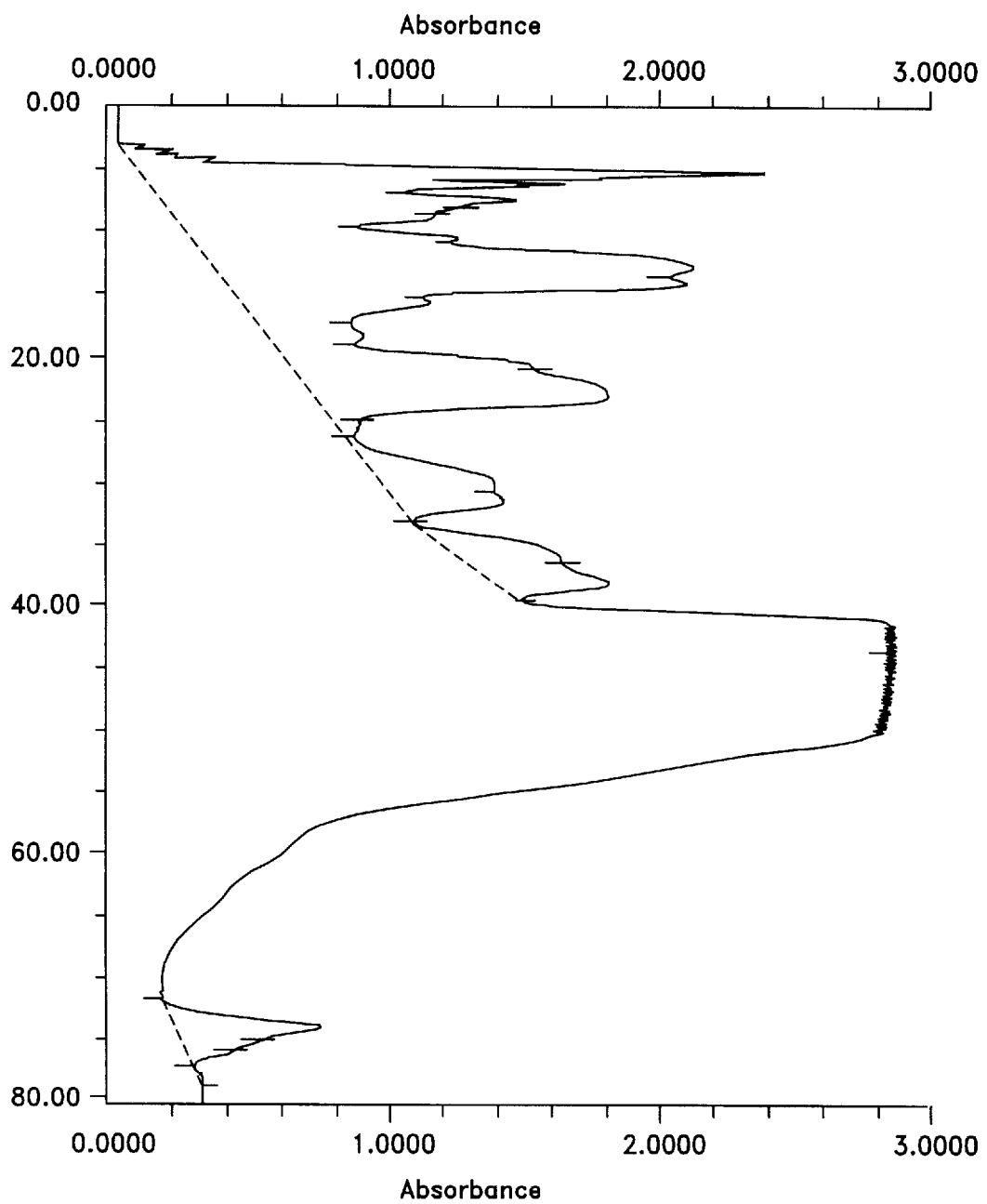
FIG. 13 depicts a chromatogram demonstrating purification of a 2'-deoxy oligomer having an alternating Rp-methyl-phosphonate-diester backbone.

Purification of 2'-Deoxy, Alternating Rp-methylphosphonate-diester Backbone Oligomers A 2'-deoxy oligomer (TAGCTTCCTTAGCTCCTG) [SEQ. ID. NO. 14] containing alternating Rp-methylphosphonate and diester linkages was synthesized in a stepwise manner using chirally pure methylphosphonate dimer synthons on a Biosearch Expedite synthesizer. After deprotection with ethylenediamine and subsequent neutralization and desalting, the oligomer (236 O.D.s) was purified by normal phase chromatography on a 4.6 mm×250 mm cyclobond column (β-cyclodextrin derivatized 5µm, 60 Å ACN, 40% 200 mM NH$_4$AC, pH 5.0), at a flow rate of 1 ml/minute. Fractions eluting at 40 to 51:30 minutes were pooled to give the product full-length oligomer. FIG. 13 depicts the chromatogram obtained.

Figure 14:
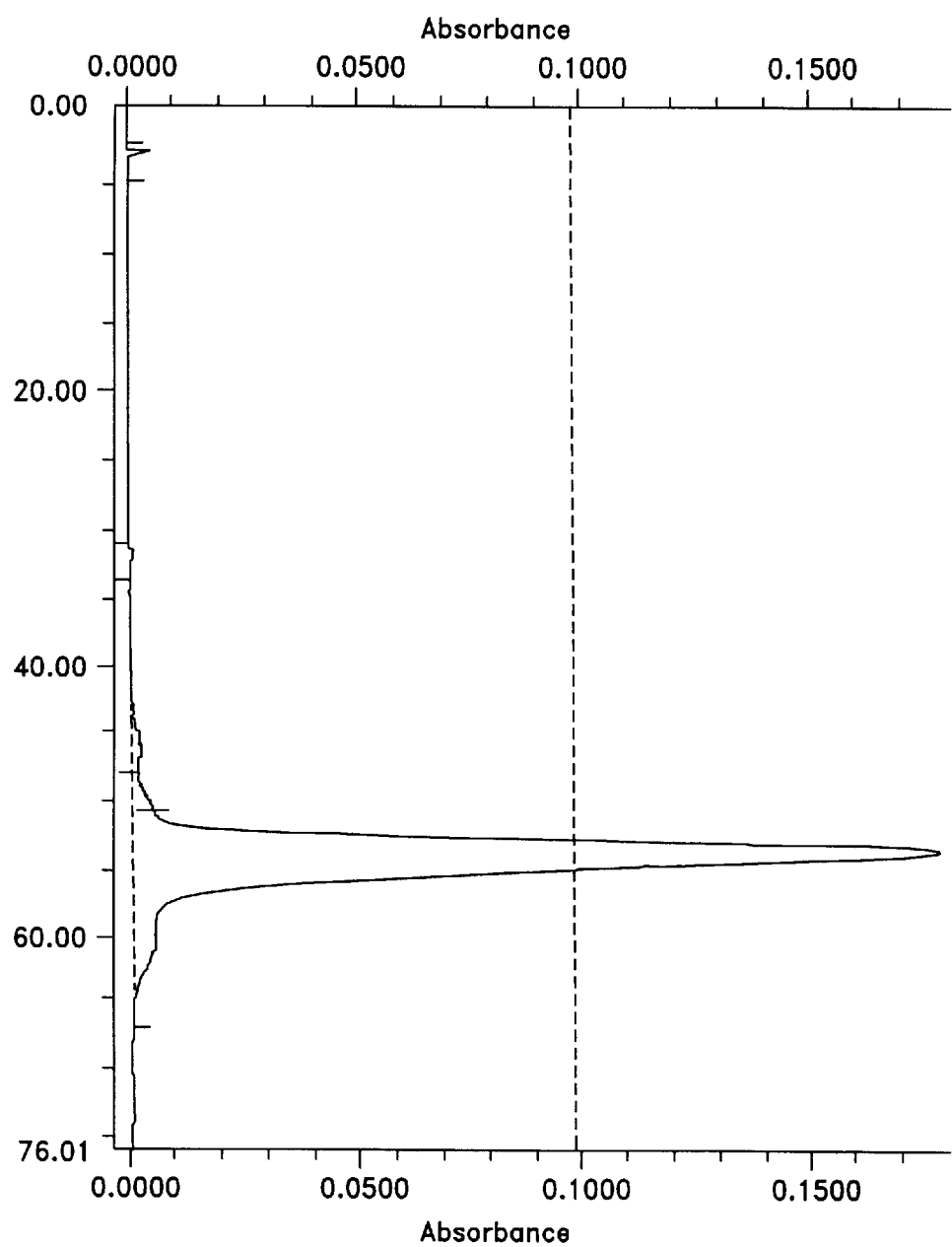
FIG. 14 depicts the confirmatory chromatogram for the oligomer of FIG. 13.

To confirm purification of the full-length oligomer, a small portion was injected on a 4.5 mm×250 mm cyclobond column (β-cyclodextrin derivatized, 5 µm, 60 Å pore spherical silica, Astec, Inc.,) which had been equilibrated with the mobile phase (60% ACN, 40% 100 mM NH$_4$Ac, pH 5.0). The method was run isocratically with the above conditions. The retention time of full length oligonucleotide was 54.3 min. FIG. 14 depicts the chromatogram obtained.

Example 15

Figure 15:
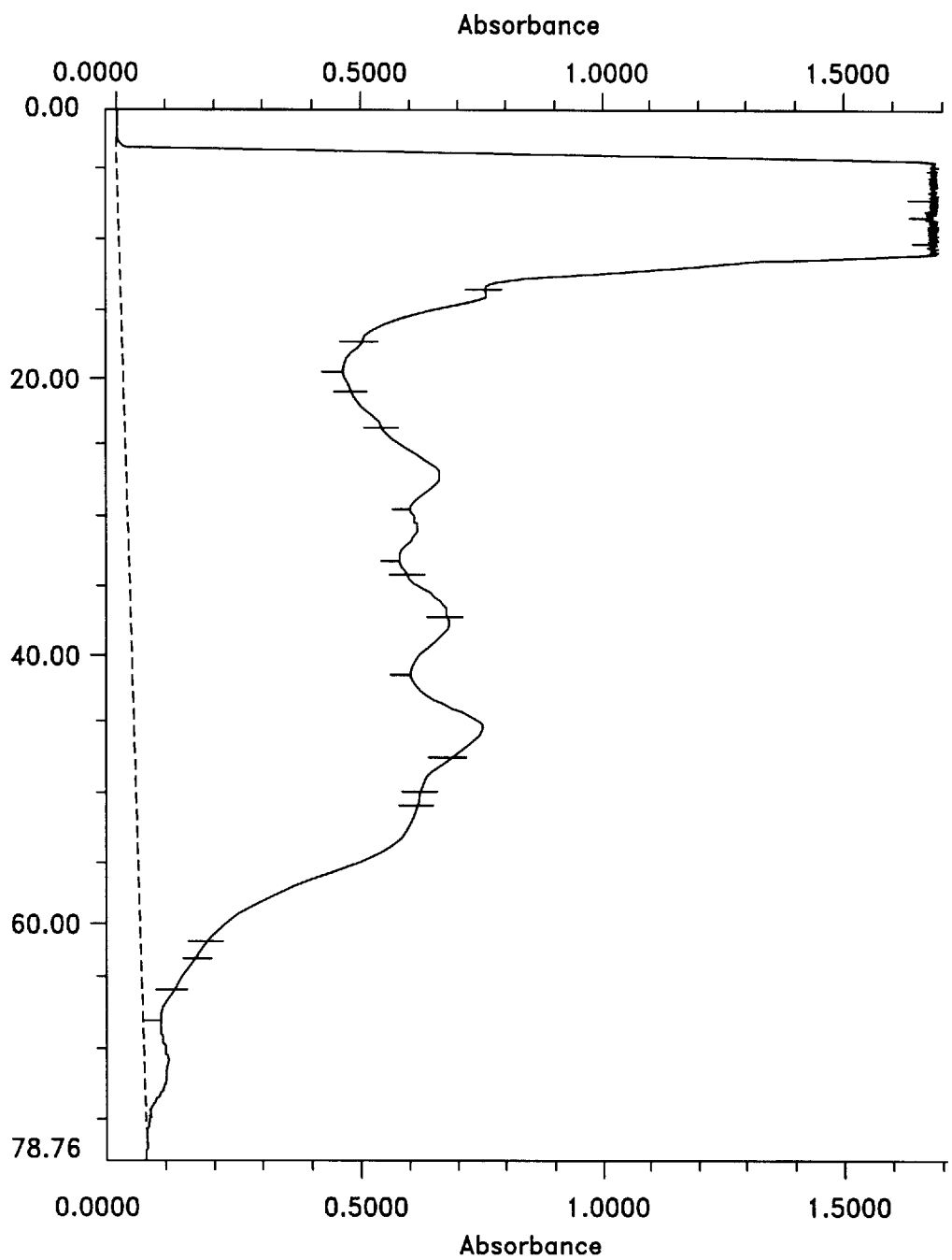
FIG. 15 depicts a chromatogram demonstrating purification of a 2'-O-methyl oligomer having an alternating Rp-methylphosphonate-diester backbone with a phosphorothioate core.

Purification of 2'-O-methyl Alternating Rp-methylphosphonate-diester Backbone Oligomer With a Phosphorothioate Core A 2'-O-methyl oligomer [CUUGGCUA(TTGCTT) CCAUCUT] [SEQ. ID. NO. 15] containing alternating Rp-methyphosphonate and diester linkages with a core of phosphorothioate linkages (indicated by parentheses) was synthesized in a stepwise manner using chirally pure methylphosphonate dimer synthons and β-cyanoethyl amidite monomers on a Pharmacia Oligopilot. After deprotection with ethylenediamine and subsequent neutralization and desalting, the oligomer (about 260 O.Ds) was purified by normal phase chromatography on a 4.6 mm×250 mm cyclobond column (β-cyclodextrin derivatized, 5 μm, 60 Å pore, spherical silica), which had been equilibrated with the mobile phase (57% ACN, 43% 100 mM $NH_4Ac$, pH 5.0) at a flow rate of 1 ml/minute. Fractions eluting at 14:45 to 25 minutes were pooled to give the product full length oligomer. FIG. 15 depicts the chromatogram obtained.

Figure 16:
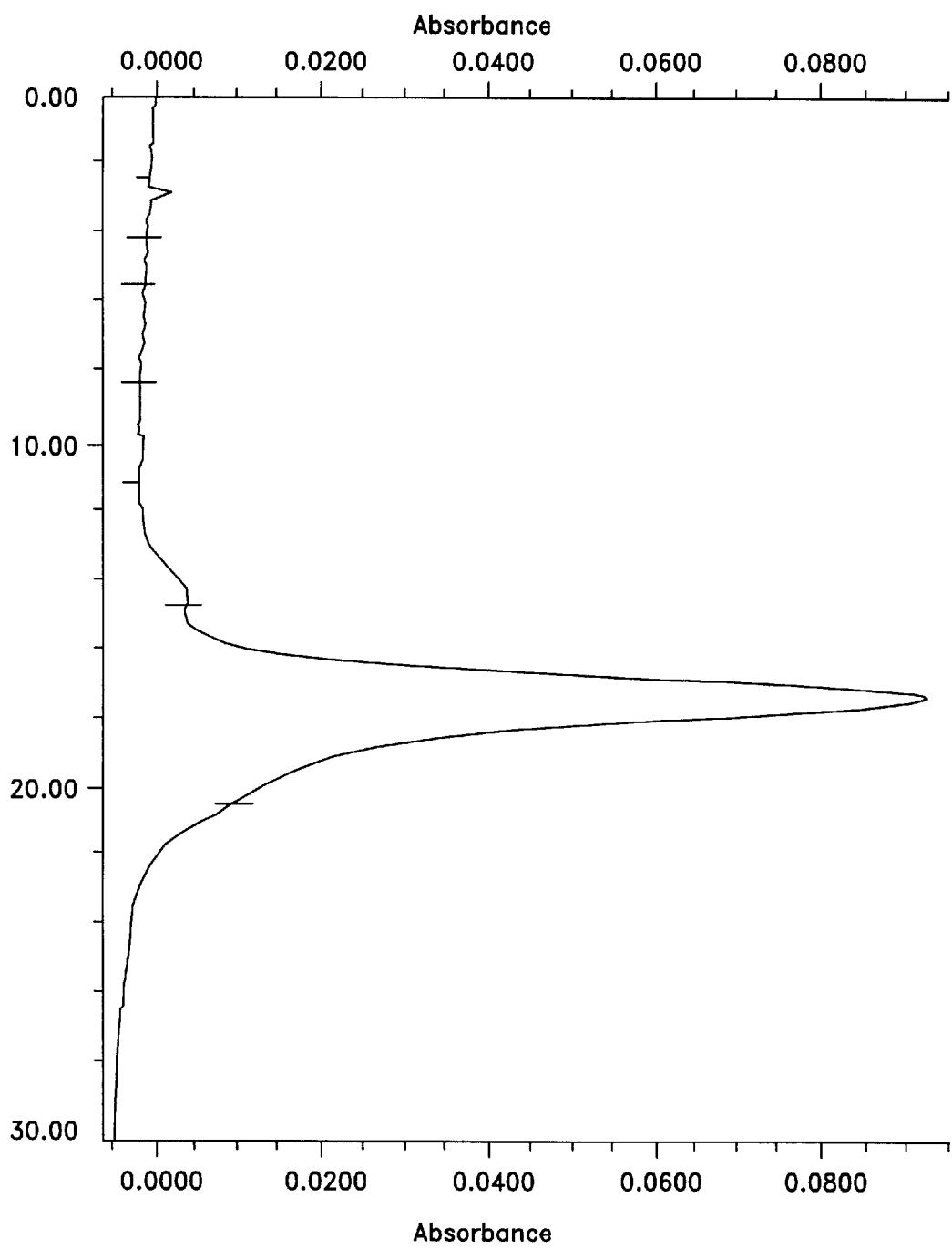
FIG. 16 depicts the confirmatory chromatogram for the oligomer of FIG. 15.

To confirm purification of the full length oligomer, a small portion was injected on a 4.5 mm×250 cyclobond column (β-cyclodextrin derivatized, 5 μm, 60 Å pore, spherical silica, Astec, Inc.) which had been equilibrated with the mobile phase (55% ACN, 45% 100 mM $NH_4Ac$, pH 5.0). The method was run isocratically with the above conditions. The retention time of full length oligonucleotide was 17.4 min. FIG. 16 depicts the chromatogram obtained.

Example 16

Figure 17:
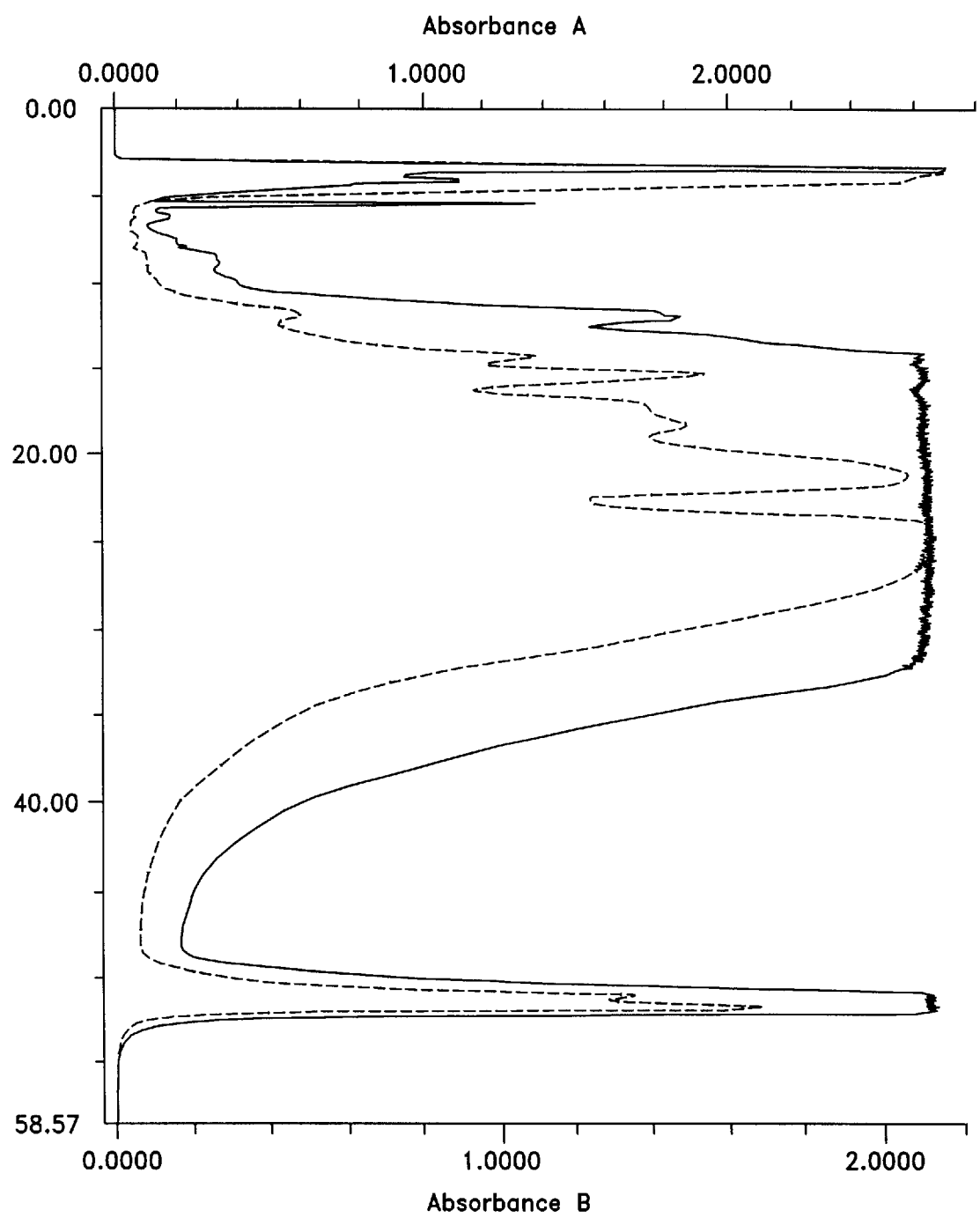
FIG. 17 depicts a chromatogram demonstating purification of a 2'-deoxy oligomer having an alternating Rp-methylphosphonate-phosphorothioate backbone.

Purification of 2'-Deoxy Alternating Rp-methylphosphonate-phosphorothioate Backbone Oligomers A 2'-deoxy oligomer (GTCTTCCATGGATGTTGT) [SEQ. ID. NO. 16] containing alternating Rp-methylphosphonate and phosphorothioate linkages was synthesized in a stepwise manner using chirally pure methylphosphonate dimer synthons on a Biosearch Expedite synthesizer. After deprotection with ethylenediamine and subsequent neutralization and desalting, the oligomer (about 104 $O.D._5$) was purified by normal phase chromatography on a 4.6 mm×250 mm cyclobond column (β-cyclodextrin derivatized, 5 μm, 60 Å pore, spherical silica) which had been equilibrated with the mobile phase (65% ACN, 35% 100 mM $NH_4Ac$, pH 6.0) at a flow rate of 1 ml/minute. Fractions eluting at 21:30 to 27 minutes were pooled to give the product full length oligomer. FIG. 17 depicts the chromatogram obtained.

Figure 18:
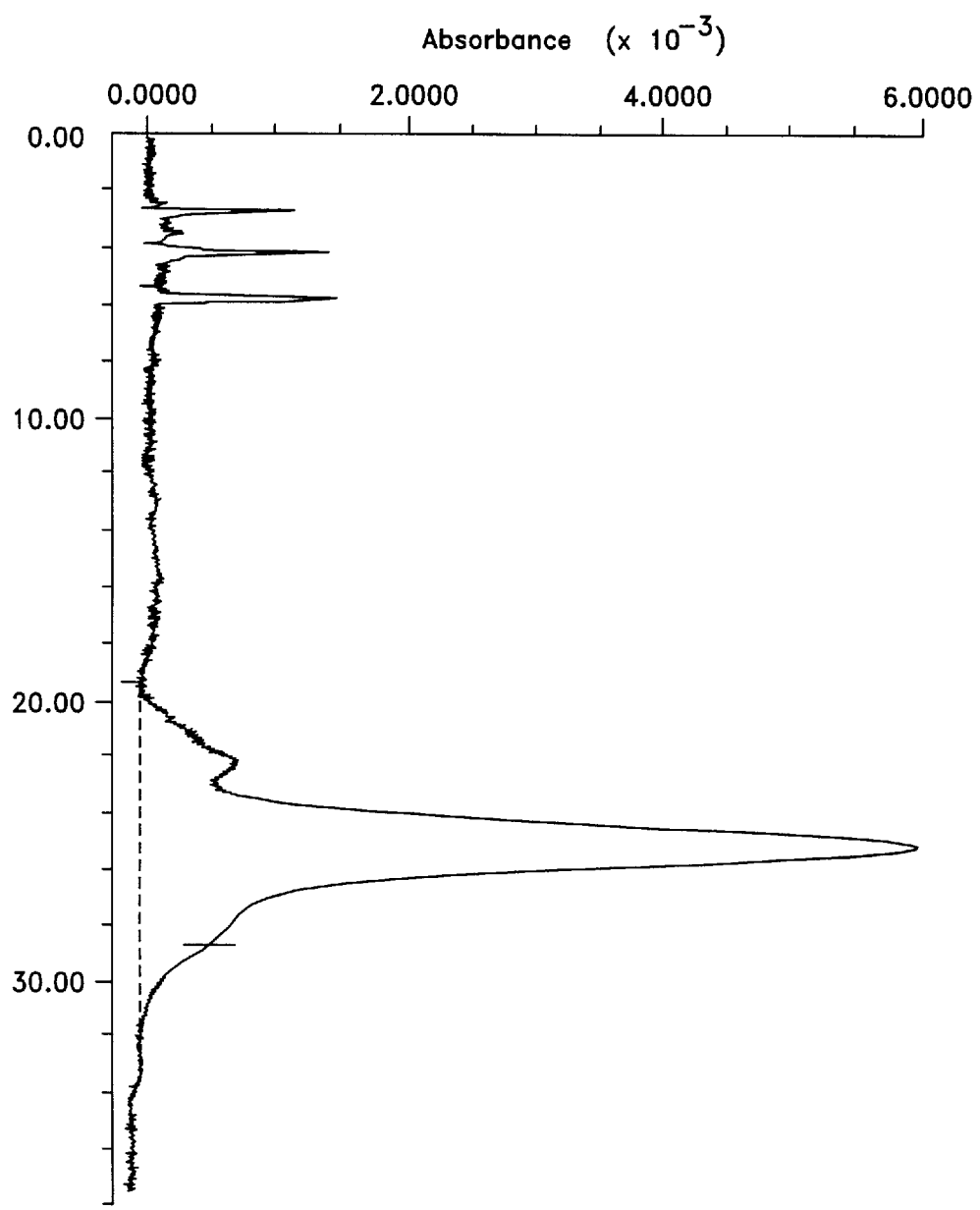
FIG. 18 depicts a confirmatory chromatogram for the oligomer of FIG. 17.

To confirm purification of the full length oligomer, a small portion was injected on a 4.5 mm×250 mm cyclobond column (β-cyclodextrin derivatized, 5 μm, 60 Å pore, spherical silica, Astec, Inc.) which had been equilibrated with the mobile phase (65% ACN, 35% 100 mM $NH_4Ac$, pH 6.0). The method was run isocratically with the above conditions. The retention time of full length oligonucleotide was 25.2 min. FIG. 18 depicts the chromatogram obtained.

Example A

Preparation of MP($R_p$)/DE and MP($R_p$)/MP Dimer Synthons

1. Preparation of a (CT) Dimer Having a Chirally Pure Methylphosphonate Internucleosidyl Linkage Using Solution Phase Chemistry Into a 2 L roto-evaporator flask was placed 10.0 g (28 mM) of 3'-tert-butyldimethylsilyl thymidine and 26.1 g (35 mM) of 5'-dimethoxytrityl-$N^4$-isobutyryl-3'-methyl-N,N-diisopropylaminophosphoramidite-2'-deoxycytidine. The solids were dissolved in 500 ml of acetonitrile and evaporated to dryness under vacuum. This process was repeated with another 500 ml of acetonitrile and then the flask was released under argon and stoppered with a rubber septa.

This dry solid foam was then dissolved in 500 ml of acetonitrile ("ACN"), and with manual stirring, treated all at once with 404 ml tetrazole (180 mM, 0.45M tetrazole in THF). Manual stirring is continued for 30 seconds and then the flask is allowed to stand for another 2.5 minutes, after which time the reaction mix is treated all at once with 275 ml of an oxidizer solution ($I_2/H_2O$/lutidine/THF; 25 g/2.5 ml/100 ml/900 ml). The solution was stirred manually and allowed to stand at room temperature for 15 minutes. The resulting dark amber solution was then treated with bisulfite (2 g/25 ml $H_2O$), which upon addition, turned the solution light amber as it reacted with the excess iodide. The reaction mix was then concentrated to a thick oil and taken up in ethyl acetate ("EtOAc") (500 ml) and washed with saturated sodium bicarbonate (2×250 ml) and $H_2O$ (2×250 ml). The organic phase was dried over $MgSO_4$, filtered and concentrated to a light colored solid foam, which upon further drying yielded 35 grams of crude dimer.

The crude dimer was run on HPLC (reverse phase, Waters C18 bondapak) with a program (ACNMETH) starting with 50% acetonitrile and 0.1M triethylammonium acetate (TEAA, pH~7.0) which increased to 100% acetonitrile over 20 minutes with a linear gradient. Two major peaks were resolved, one at 4.5 minutes, which is residual lutidine and the other at 14.5 minutes which is the mixture of $R_p$ and $S_p$ diastereomers. The ratio of $R_p$ and $S_p$ was determined quantitatively by taking a 5 mg aliquot of the crude product and dissolving it in 1.5 ml of acetonitrile along with 0.5 ml of tetrabutylammonium fluoride (TBAF, 1M solution in THF). After standing at room temperature for 10 minutes the sample was run on HPLC. Two new peaks were observed at 6.5 and 7.1 minutes and the later eluting peak was gone. The first new peak, which is believed to be the $S_p$ diastereomer, represented 66% (2/1) of the normalized value for the two peaks. The crude product was also analyzed by the (normal phase silica plate) in 75/25 EtOAc/$CH_2Cl_2$ ("175/25") with 5% methanol added. The tlc showed two spots with Rf's of 0.45 and 0.64, respectively; the faster running product (believed to be the $R_p$ form) was less intense than the slower moving one.

The $R_p$ diastereomer was separated on normal phase silica using a methanol step gradient in 75/25 EtOAc/$CH_2Cl_2$. A 7.5 cm by 60 cm column, was loaded with 700 g of silica (first slurried in 2.5 L of neat 75/25 EtOAc/$CH_2Cl_2$). The crude dimer was then dissolved in 75 ml of 75/25 EtOAc/$CH_2Cl_2$ and loaded onto the column. The column was started with 1% methanol and increased to 2% and finally 3% where the $R_p$ dimer began to elute. The $R_p$ dimer eluted cleanly over several bed volumes while maintaining 3% methanol in the eluent. The $S_p$ dimer was eluted later with 30% methanol. The $R_p$ dimer yield was 11.0 grams, while the $S_p$ yield was 17.8 grams. HPLC analysis (ACNMETH) was performed on the $R_p$ dimer and one peak was observed at 14.5 minutes. The tlc (75/25 EtOAc/$CH_2Cl_2$, 5% methanol) of this product, revealed a single spot product with an Rf of 0.55 which, upon treatment with 10% sulfuric acid in ethanol and heat, was both trityl and sugar positive.

The newly resolved $R_p$ dimer, 11.0 g (0.011M) was dissolved in 110 ml of ACN and treated all at once at room temperature with 22 ml of TBAF (0.022M, 1M in THF). The reaction mixture was allowed to stand overnight at ambient temperature. The next morning the reaction was determined to be complete by tlc (75/25, EtOAc/$CH_2Cl_2$ with 10% methanol); no starting material was detected but a small amount of 5'-DMT-dT was observed, which runs considerably faster on normal phase silica than the 3'-OH of the dimer. The reaction mixture was concentrated on a rotary evaporator to a thick oil which was then dissolved in $CH_2Cl_2$ (200 ml) and washed with saturated sodium bicarbonate (2×100 ml) and $H_2O$ (2×100 ml). The organic phase was dried over $MgSO_4$, filtered, and concentrated to a light yellow solid foam, which was purified on 100 grams of silica (75/25, EtOAc/$CH_2Cl_2$ with 5% methanol). The 5'-DMT-dT was removed but an impurity at 13.5 minutes (HPLC, ACNMETH) was detected which was first believed to be unreacted starting material (t-BDMS on) but after additional treatment with TBAF this was found not to be the case. A second column, using 100 g of silica and the same eluent was run and smaller fractions were taken; the column was able to successfully separate the two spots. The pure CT-$R_p$ dimer fractions were pooled and concentrated to yield 5.5 grams of a nearly white solid foam.

2. Preparation of a Chirally Pure (CT) MP($R_p$)/DE Dimer Synthon

Into a 100 ml round bottom flask was placed 0.5 g (0.55 mMol) CT-3'-OH dimer (product of Example A1) which was rendered anhydrous by 3×20 ml co-evaporations with pyridine. The flask was released from the vacuum system under argon gas and stoppered with a rubber septa. The compound was redissolved in 10 ml acetonitrile and 200 μl (1.4 mMol, 2.5 eq) TEA were added. To the resulting mixture at room temperature with manual stirring, was added in one portion 200 μl (0.90 mmol, 1.6 eq.) 2'-cyanoethyl-N,N-diisopropylchlorophosphoramidite. The reaction mixture was allowed to sit at room temperature before being analyzed by reverse phase HPLC. The HPLC (Beckman System Gold, C18 bondapak, ACN method Solution A was 50/50 ACN/0.1M TEAA in water, pH 7 and Solution B was ACN. A gradient of 0 to 100% Solution B was run at a rate of 1 ml/minute over 25 minutes) showed complete conversion of starting material and a crude purity of greater than 90 percent. The diastereomers of the phosphoramidite were not resolved. The reaction mixture was concentrated under vacuum to a light yell solid foam. The foam was purified immediately by chromatography on 20 g of normal flash grade silica equilibrated with 5/1/5 ethyl acetate/acetonitrile/methylene chloride with 2% TEA to give 0.5 g (82% yield) of the above-identified product as an off-which solid foam having a purity of 99.3% as determined by HPLC.

3. Preparation of a Chirally Pure (CT) MP($R_p$)/MP Dimer Synthon

The CT-3'-OH dimer, 5.5 g (6 mM), prepared as described in part 1 above, was rendered anhydrous with two co-evaporations with pyridine. The resulting solid foam was released from the rotary evaporator with argon and stoppered with a rubber septa. The solid foam was dissolved in 100 ml of 9/1, ACN/$CH_2Cl_2$, then treated with 1.7 ml triethylamine (TEA, 12 mM). With magnetic stirring, the reaction mix was treated dropwise at room temperature with 1.5 ml chloromethyl-N,N-diisopropylamino phosphine (Cl-MAP, 8 mM). The reaction was monitored on HPLC (ACNMETH) and after 1.5 hours was complete, showing two main products, one at 3.5 minutes which was pyridine and a second at 14.3 minutes which was the desired amidite.

The reaction mixture was concentrated on a rotary evaporator using a partial vacuum; the flask which contained the resulting light amber sludge was released under argon and capped. The crude product was immediately passed through a flash column containing 60 grams of silica (first equilibrated in 1/1/1 ACN/EtOAc/$CH_2Cl_2$ with 3% TEA). The product was eluted quickly with this eluent and all U.V. positive fractions were pooled and concentrated. The resulting solid foam was co-evaporated with ACN to remove any residual TEA, then dried overnight under full vacuum. The final product, an off white solid foam, weight 5.0 grams.

Example B

Preparation of (CU) 2'-O-Methyl MP($R_p$)/2'-O-Methyl DE and 2'-O-Methyl MP($R_p$)/2'-O-Methyl MP Dimer Synthons 1. Preparation of 2'-O-Methyl C Monomer A 5.0 g (8 mmol) portion of 2'-O methyl cytidine was rendered anhydrous with pyridine co-evaporations (3×25 ml) and then dissolved in 50 ml acetonitrile. The solution was treated with 1.65 ml triethylamine ("TEA") (12 mmol, 1.5 eq.) and cooled in an ice bath. The solution was then treated with dropwise addition of 1.65 ml chloromethyl-N, N-diisopropylamino phosphine ("Cl-MAP") over two minutes. The ice bath was removed and the reaction mixture stirred for two hours. The reaction mixture (reaction was determined to be complete by HPLC) was concentrated to dryness. The residue was dissolved in 20 ml ethyl acetate/heptane (1:1) with 4% TEA, then loaded onto 40 g silica gel equilibrated with the same solvent system. All UV absorbing eluent from the column was collected and pooled, then concentrated to give 5.5 g of the above-identified product (yield about 90%).

2. Preparation of Silyl-Protected 2'-O-Methyl Uridine

Into a 250 ml round bottom flask was placed 5.0 g (9.0 mmol) 5'-DMT, 2'O-methyl uridine which was rendered anhydrous with dimethylformamide (DMF) co-evaporations (3×25 ml). The resulting dry foam was taken up in 50 ml DMF, then treated all at once with 2.4 g (35 mmol, 3.9 eq.) imidazole, followed by dropwise addition of 3.0 ml (12 mmol, 1.3 eq.) t-butyldiphenylsilyl chloride. The reaction mixture was stirred at room temperature overnight.

The progress of the reaction was checked by HPLC (ACN method (Solution A was 50/50 ACN/0.1M TEAA in water, pH 7 and Solution B was ACN; a gradient of 0 to 100% Solution B was run at a rate of 1 ml/minute over 25 minutes) and thin layer chromatography ("TLC") using 5% methanol in methylene chloride, and determined to be complete (no starting material was evident). The reaction mixture was then poured into ice water and taken up in methylene chloride, then washed several times with aqueous sodium bicarbonate and water. The organic phase was dried over magnesium sulfate, filtered and then concentrated to give 7.2 g of a solid foam which gave a single spot on TLC. The solid foam was then dissolved in 70 ml methylene chloride and treated (with rapid magnetic stirring) all at once with 70 ml benzene sulfonic acid, 2% by weight in 2:1 methylene chloride/methanol. After stirring for 15 minutes at room temperature, the reaction mixture was quenched with 10 ml TEA. The resulting detritlylated compound was stripped down to a thick amber oil which was then loaded onto 150 g. silica gel equilibrated in heat methylene chloride. The product was eluted from the column using 2% methanol (in methylene chloride). After drying, 3.51 g of the above identified product were obtained (yield about 80%).

3. Preparation of (CU) 2'-O-Methyl MP($R_p$)/2'-O-Methyl DE Dimer

The silyl-protected 2'-O-methyl uridine monomer (product of Example 2B) (3.0 g, 6 mmol) was taken up in 30 ml anhydrous ACN. The 2'-O methyl cytidine amidite monomer (product of Example B1) (5.5 g, 7 mmol, 1.2 eq.) separately, was taken up in 55 ml ACN. Both solutions were allowed to stand over 3 Å molecular sieves overnight at room temperature.

The two solutions were carefully decanted into a single flask and treated with 94 ml tetrazole (0.45M in ACN, 42 mmol, 7 eq). The resulting mixture was stirred for 4 minutes and then oxidized by addition of 1.5 ml (1.2 eq.) cumene hydroperoxide. The reaction mixture was concentrated to dryness, then taken up in methylene chloride and washed with aqueous sodium bicarbonate and water. The organic phase was dried over magnesium sulfate, filtered and concentrated to give 7.5 g. of a solid foam. The diastereomeric ratio as determined by HPLC by comparison of areas under peaks was 57/43 $S_p$ to $R_p$.

The $R_p$ diastereomer was isolated by column chromatography using two silica columns (100:1, silica to crude product, equilibrated in 3:1 ethylacetate/methyl chloride with an increasing methanol gradient from 1 to 5%). A total of 1.07 g of pure $R_p$ dimer was isolated.

4. Deprotection of (CU) 2'-O-Methyl Dimer

A 1.07 g (0.90 mmol) portion of the 2'-O methyl CU dimer (product of Example B3) was dissolved in 10 ml THF and treated all at once with 1.5 ml (1 m in THF, 1.5 eq.) tetrabutylammonium fluoride ("TBAF"). The reaction mixture was stirred at room temperature of r 30 minutes after which time HPLC revealed complete deprotection of the silyl group had been achieved. The reaction mixture was concentrated and the concentrate purified on 10 g silica gel, eluting with 3:1 ethyl acetate/methylene chloride with 5% methanol. The clean fractions were concentrated to give 550 mg of the above-identified pure 5'-OH dimer.

5. Preparation of a Chirally Pure (CU) 2'-O-Methyl (MP/DE) Dimer Synthon

A 230 mg portion of 2'-O-methyl CU 3'-OH dimer (product of Example B4) was rendered anhydrous by 2×5 ml co-evaporations in ACN. The resulting dry solid foam was dissolved in 2.5 ml ACN and then 73 µl (2.5 eq.) triethylamine ("TEA") and 94 µl (2.0 eq.) 2'-cyanoethyl-N,N-diisopropyl chlorophosphoramidite (βCNE) were added. The reaction mixture was stirred at room temperature for 2 hours at which time HPLC analysis determined the reaction to be complete. The reaction mixture was dissolved in eluent (3/1/1 ethylacetate/acetonitrile/methylene chloride with 4% TEA) and loaded onto 2 g silica gel equilibrated with 3/1/1 ethyl-acetate/acetonitrile/methylene chloride with 4% TEA. The column was run using 3/1/1 ethylacetate/acetonitrile/methylene chloride with lo TEA. The clean fractions, 3 to 25, were concentrated, redissolved in acetonitrile and concentrated again to a solid foam. The foam was dried overnight under full vacuum to give 200 mg of the above-identified product.

6. Preparation of Chirally Pure (CU) 2'-O-Methyl MP ($R_p$)/2'-O-Methyl MP Dimer Synthon Into a 100 ml round bottom flask was placed 400 mg (0.372 mmole) of 2'-O methyl CU dimer (product of Example B4); it was rendered anhydrous by 1×5 ml co-evaporation with acetonitrile. The dry foam was then released from the vacuum system under argon gas, dissolved in 4 ml ACN and stoppered with a rubber septa. The solution was treated with 2 equivalents TEA (103 µl, 0.744 mmol), followed by 1.75 equivalents chloro-methyl-N,N-diisopropyl phosphine ("Cl-MAP") (118 µl, 0.651 mmol). The reaction mixture was stirred for 1 hour at room temperature, after which time HPLC showed about 50/50 starting material/product. An additional 50 µl TEA and 70 µl Cl-MAP were then added and the mixture stirred for an hour. When HPLC showed only 80% conversion, an additional 30 µl TEA and 30 µl Cl-MAP were added and the resulting mixture stirred another hour. At this time HPLC revealed 6% starting material. The reaction mixture was concentrated to dryness. The residue was dissolved in 500 ml 3/1/3 ethylacetate/acetonitrile/methylene chloride with 4% TEA and loaded onto 5 g silica equilibrated in the same solvent system. Fractions were collected. The early fractions were contaminated with a yellow impurity and, thus, were pooled and concentrated separately. The product from those fractions was then repurified by chromatography using the same conditions and pooled with the clean product isolated from the first column. The combined products were co-evaporated with ACN (3×5 ml) and dried overnight under full vacuum to give 350 mg (77% yield) of the above identified product which HPLC showed to be 95.5% pure.

Example C

Preparation of 2'-O-Methyl MPS($R_p$)/2'-O-Methyl-DE and 2'-O-Methyl MPS($R_p$)/2'-O-Methyl-MP Dimer Synthons These dimer synthons are prepared by following the procedures described in Example B, except that in Paragraph 3, an equivalent amount of 3 H-1,2-benzodithiole-3-one, 1,1-dioxide (Beaucage reagent) is substituted for cumene hydroperoxide. The procedures of Paragraphs 2E and 2F, respectively, lead to the phosphodiester and methylphosphothioate linkage combinations.

Example D

Preparation of MPS($R_p$)/DE Dimer Synthons

These dimer synthons are prepared by following the procedures of Example A, except in Paragraph 1, an equivalent amount 3-H-1,2-benzodithiole-3-one, 1,1-dioxide (Beaucage reagent) is substituted for the oxidizer solution ($I_2$/$H_2O$/lutidine/THF).

Example E

Preparation of MP($R_p$)/PS2 Dimer Synthons

The MP($R_p$)/PS2 dimer synthons are prepared as follows. Isometrically pure $R_p$ dinucleosides having a free 3'-OH are prepared according to the methods described in Example 1A. The dinucleoside is converted to the corresponding thiophosphoramidite using procedures such as those of Plotto et al. (Plotto et al, tetrahedron 47:2449–61 (1991)) or Gorenstein et al., U.S. Pat. No. 5,218,088. The dinucleoside is co-evaporated three times with anhydrous pyridine, followed by three co-evaporations with toluene. A portion of dinucleoside (10 mmoles) is dissolved in 200 ml anhydrous dichloromethane, then three equivalents of anhydrous diisopropylethylamine followed by 1.5 equivalents of chloro-N,N-diisopropylaminothiomethoxyphosphine are added at 0° C. with stirring. The reaction is monitored by TLC until determined to be complete.

The product is worked up and purified using the procedures of Example A2 for isolation of the MP($R_p$)/DE phosphoramidite.

Example F

Preparation of MPS($R_p$)/PS2 Dimer Synthons

The MPS($R_p$)/PS2 dimer synthons are prepared as follows. The isometrically pure $R_p$ dinucleoside with a free 3'-OH is prepared according to the methods of Example D. Using the dinucleoside, the dimer synthon is prepared by the methods of Example E.

Example G

Preparation of MPS($R_p$)/2'-O Methyl DE Dimer Synthons

The MPS($R_p$)/2'-O-methyl DE dimer synthons are prepared using procedures analogous to those of Examples A and C but using the appropriate protected 2'-deoxynucleoside and protected 2'-O-methyl nucleosides.

Example H

Preparation of a Poly-CT Oligomer Having Alternating MP($R_p$)/DE Internucleosidyl Linkages An oligomer having the sequence 5'-(C*T)-(C*T)-(C*T)-(C*T)-(C*T)-(C*T)-(C*T)-A-3' [SEQ. ID. NO. 1] was prepared using a C*T MP($R_p$)/DE dimer synthon prepared according to Example 1. The grouped dinucleosides indicate where the stereochemistry is fixed as the fast eluting isomer on silica gel (putative $R_p$) and the asterisks indicate the chirally pure linkages.

Manual couplings were used to synthesize the oligomer to conserve reagent, although the process can be done on an automated DNA synthesizer. The sequence was synthesized from the 3'-terminus starting with methacrylate support bound deoxyadenosine.

The protected dinucleoside methylphosphonamidite (22 mg each per required coupling) freshly co-evaporated with pyridine and toluene to ensure dryness were placed into dried 1 ml glass autosampler vials and dissolved in anhydrous acetonitrile to a concentration of 0.1M (200 µl per coupling). The vessels were purged with argon and tightly sealed with screw caps with teflon septa.

A 1 µmole scale DNA synthesis column (Milligen) was filled with 1 µmole of methacrylate support bound deoxyadenosine. The column was attached to a ring stand in a vertical orientation. A male-male luer fitting was attached to the bottom along with an 18 gauge needle to control the effluent. The column was washed with 10 ml acetonitrile using a syringe. The support bound nucleoside was detritylated by passing 3 ml of 2% dichloroacetic acid in dichloromethane through the column over 1.5 minutes. The orange, dimethoxytrityl cation bearing solution was reserved. The column was washed twice with 10 ml each of anhydrous acetonitrile.

The first coupling was accomplished as follows: 10 ml more anhydrous acetonitrile was passed through the column. Then, 200 µl of the CT methylphosphonamidite was drawn into a 1 ml syringe. Next, 200 µl of 0.45M tetrazole in anhydrous acetonitrile was likewise drawn into the syringe containing the methylphosphonamidite. The reagents were rapidly mixed in the syringe, then slowly passed through the column dropwise over three minutes, being sure to lightly draw the plunger up and down to ensure adequate mixing with the support. After 3 minutes, 1 ml of the oxidizing reagent (0.1M $I_2$ in 73% tetrahydrofuran, 25% 2,6-lutidine and 2% water) was passed through the column over one minute. The column was washed with 20 ml acetonitrile and then treated with 600 µl of a solution containing 20% (v/v) acetic anhydride, 30% (v/v) acetonitrile, 50% (v/v) pyridine and 0.312% (w/v) dimethylaminopyridine. The column was then washed with 20 ml acetonitrile.

The above-described synthetic cycle was repeated until the synthesis was completed. The overall coupling efficiency based on dimethoxytrityl absorbance was 95.7%, for an average of 99.3% per coupling.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/$NH_4OH$ (9/9/1). Then, 1 ml of ethylenediamine was added to the reaction vessel and the reaction allowed to sit for 6 hours at ambient temperature in order to go to completion. The supernatant containing the oligomer was then removed from the support and the support was rinsed twice with 2 ml of 1/1 acetonitrile/water; the washings were combined with the supernatant. The combined solution was diluted to 30 ml total volume with water and neutralized with approximately 4 ml of 6N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column, it was washed with 30 ml of water. The product was then eluted with 5 ml of 1/1 acetonitrile/water.

Alternatively, the above-identified oligomer can be synthesized on an automated DNA synthesizer. In this case the appropriate dimer synthons (as used above in the manual synthesis) are dissolved in acetonitrile to a concentration of 0.1M as described above. The amidite solutions are placed in conical vessels on a Millipore Expedite DNA Synthesizer. All other reagents (oxidizer, deblock, capping reagents and activator) are prepared as described above for the manual synthesis, and applied to the appropriate positions on the instrument as instructed in the manual. Programming parameters for one synthesis cycle are as given in U.S. patent application Ser. No. 08/158,014. The deprotection and purification of the oligomer is carried out as for the manually synthesized oligomer.

Example I

Preparation of a Poly-CU Oligomer Having Alternating 2'-O-Methyl MP($R_p$)/2'-O-Methyl DE and 2'-O-Methyl MP($R_p$)/2-O-Methyl DE Internucleosidyl Linkages An oligomer having the sequence 5' (C*U)-(C*U)-(C*U)-(C*U)-(C*U)-(C*U)-(C*U)-A-3' [SEQ. ID. NO. 2] was prepared using 2'-O-methyl MP($R_p$)/2'-O-methyl DE dimer synthons prepared according to Example 2 hereinabove.

The appropriate dimer synthons were dissolved in acetonitrile to a concentration of 0.1M. All other reagents used were as described in Example H.

A 1 µmole scale DNA synthesis column (Millipore) was filled with 1 µmole of methacrylate support bound deoxyadenosine. The dimer synthons were coupled sequentially from the 3'-terminus as described in Example 8 except that the coupling time was extended to two minutes. The overall coupling efficiency based on dimethoxytrityl absorbance was 50%, for an average of 91% per coupling. The dimethoxytrityl group was removed from the oligomer at the end of the synthesis.

The deprotection was carried out as described in Example H. The crude yield was 103 OD$_{260}$ units. The oligomer was purified on HPLC with a Beckman Ultrasphere-R$_p$ using an increasing gradient of acetonitrile in 0.5M triethylammonium acetate (10% to 30% over 30 minutes). The isolated yield was 39 OD$_{260}$ units (38%). The compound was characterized by electron spray mass spectrometry (calc. 4713/found 4712).

This oligomer can also be synthesized on an automated DNA synthesizer as follows. The appropriate dimer synthons (as used above in the manual synthesis are dissolved in acetonitrile as described in Example H. The amidite solutions are placed in conical vessels on the Millipore Expedite DNA synthesizer. All other reagents (oxidizer, deblock, capping reagents and activator) are prepared as described in Example H, and are applied to the appropriate positions on the instrument as instructed by the manual. The same coupling program as described in Example H is used except that the coupling time is extended to 2 minutes.

The deprotection is carried out as described in Example H. The oligomer can be purified on HPLC using as described above for the manual synthesis.

Using similar procedures as described in detail in Example H of U.S. patent application Ser. No. 08/154,013, the oligomer 5'-(C*U)-(C*U)-(C*U)-(C*U)-(C*U)-(C*U)-(C*U)-A-3' having 2'-O-methyl MP(R$_p$)/2'-O-methyl MP (racemic) mixed linkages was prepared. The product was also characterized by electron spray mass spectroscopy (calc. 4699.5/found 4701). Automated synthesis may also be employed as explained above.

Example J

**Preparation of 5'-(T*A)-(G*C)-(T*T)-(C*C)-(T*T)-(A*G)-(C*T)-(C*C)-(T*G)-C-3' [SEQ. ID. NO. 3] Having Repeated MP(R$_p$)/MP Linkage Structures**

The grouped dinucleosides indicate coupled dimers and the asterisk indicates where the stereochemistry is fixed (chirally defined or chirally pure) as the fast eluting isomer on silica gel (identified as R$_p$).

An oligomer having this sequence was synthesized using the appropriate protected dinucleotide methylphosphonamidites prepared using methods such as those described in Examples 1A and 1C above. Manual couplings were used to synthesize the oligomer to conserve reagent, although the process can be done on an automated DNA synthesizer from the 3' terminus starting with support-bound cytidine.

Each of the desired protected dinucleotide methylphosphonamidites (22 mg each per required coupling), T*A, G*C, T*T (2×), C*C (2×), A*G, C*T, and T*G, freshly co-evaporated with pyridine and toluene to ensure dryness, was placed into a dried 1 ml glass autosampler vial and dissolved with anhydrous acetonitrile to give a concentration of 0.1M (200 μl were used per coupling). The vials were purged with argon and tightly sealed with screw caps with teflon septa.

A 1 μmole scale Milligen DNA synthesis column was filled with 1 μmole of support bound cytidine. The column was attached to a ring stand in a vertical orientation. A male-male leur fitting was attached to the bottom along with an 18 geffluent. The control the effluent. The column was washed with 10 ml of ACN using a syringe. The support bound nucleoside was then detritylated by passing 3 ml of 2% dichloroacetic acid in dichloromethane through the column over 1.5 minutes. The orange, dimethoxytrityl cation bearing solution was reserved. The column was washed twice with 10 ml each of ACN (anhydrous).

The first coupling was accomplished by passing 10 ml more ACN (anhydrous) through the column. Then, 200 μl of the TG methylphosphonamidite was drawn into a 1 ml syringe. Next, 200 μL of 0.45M tetrazole in anhydrous ACN was likewise drawn into the syringe containing the methylphosphonamidite. The reagents were rapidly mixed in the syringe, then slowly passed through the column dropwise over 3 minutes, being sure to lightly draw the plunger up and down to ensure adequate mixing with the support. After 3 minutes, 1 ml of the oxidizing reagent (0.1M I$_2$ in 74.25% THF, 25% 2,6-lutidine, and 0.25% water) as passed through the column over 1 minute. The column was then washed with 20 ml of ACN. The column was then treated for 1 minute with 600 μl of a solution containing 20% (v/v) acetic anhydride, 30% (v/v) ACN, 50% (v/v) pyridine, and 0.312% (w/v) dimethyaminopyridine. The column was washed with 20 ml of ACN.

The synthetic cycle was then repeated with each dinucleotide methylphosphonamidite until the synthesis was completed. The order of addition of dimers after the initial T*G coupling was C*C, C*T, A*G, T*T, C*C, T*T, G*C, and T*A.

The dimethoxytrityl group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/NH$_4$OH (9/9/1). Then, 1 ml of ethylenediamine was added to the reaction vessel and the reaction mixture allowed to sit for 6 hours at ambient temperature in order to go to completion. The supernatant containing the oligomer was then removed from the support and the support was rinsed twice with 1 ml of 1/1 acetonitrile/water; the washings were combined with the supernatant. The combined solution was diluted to 50 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column, it was washed with 50 ml of water. The product was then eluted with 2 ml of 1/1 acetonitrile/water.

Coupling efficiencies are set forth in the table below.

| Coupling Efficiencies of Dinucleotide Methylphosphonamidites | |
|---|---|
| Dinucleotide | Coupling Efficiency |
| T*G | 99.7% |
| C*C | 90.2% |
| C*T | 91.8% |
| A*G | 85.5% |
| T*T | 97.8% |
| C*C | 83.6% |
| T*T | 100% |
| G*C | 86.2% |
| T*A | 92.4% |

Example K

**Preparation of 5'-(G*T)-(C*T)-(T*C)-(C*A)-(T*G)-(C*A)-(T*G)-(T*T)-(G*T)-C-3' [SEQ. ID. NO. 4] Having Repeated MP(R$_p$)/MP Linkage Structures**

The grouped dinucleotides indicate coupled dimers and the asterisk indicates where the stereochemistry is fixed.

This sequence was synthesized using the appropriate protected $R_p$ dinucleotide methylphosphonamidites prepared and isolated using procedures such as those described in Examples 1A and 1C above. Manual couplings were used to synthesize the oligomer in order to conserve reagent. However, if desired, the process can be done on an automated DNA synthesizer from the 3' terminus starting with methacrylate support bound 2'-deoxycytidine.

Each of the desired protected dinucleotide methylphosphonamidites (100 mg), G*T, T*T, T*G, C*A, T*G, C*A, T*C, C*T, and G*T was placed into a dried 3 ml glass conical vial and dissolved with anhydrous acetonitrile to a concentration of 0.1M. Molecular sieves (3 Å) (0.5 ml volume) were added to each vessel, the vessels purged with argon, and tightly sealed with screw caps with teflon septa. The reagents were allowed to stand overnight prior to use.

A 1 µmole scale Milligen DNA synthesis column was filled with 1 µmole of methacrylate support bound 2'-deoxycytidine. The column was attached to a ring stand in a vertical orientation. A male-male luer fitting was attached to the bottom along with an 18 gauge needle to control the effluent. The column was washed with 10 ml of ACN using a syringe. The support bound nucleoside was then detritylated by passing 3 ml of 2.5% dichloroacetic acid in dichloromethane through the column over 3.0 minutes. The orange, dimethoxytrityl cation bearing solution was reserved. The column was washed twice with 10 ml each of ACN (anhydrous).

The first coupling was accomplished by passing 10 ml more ACN (anhydrous) through the column. Then 200 µl of the G*T methylphosphoramidite was drawn into a 1 ml syringe. Next, 200 µl of 0.45M tetrazole in anhydrous ACN was likewise drawn into the syringe containing the methylphosphonamidite. The reagents were rapidly mixed in the syringe, then slowly passed through the column dropwise over 1 minute, being sure to lightly draw the plunger up and down to ensure adequate mixing with the support. After 3 minutes, 1 ml of the oxidizing reagent (0.1M $I_2$ in 74.25% THF, 25% 2,6-lutidine, and 0.25% water) was passed through the column over 1 minute. The column was then washed with 20 ml of ACN. The column was then treated for 1 minute with 600 µl of a solution containing 20% (v/v) acetic anhydride, 30% (v/v) ACN, 50% (v/v) pyridine, and 0.312% (w/v) dimethyaminopyridine. The column was washed with 20 ml of ACN.

The synthetic cycle was then repeated with each dinucleotide methylphosphonamidite until the synthesis was completed. The order of addition of dimers after the initial G*T coupling was T*T, T*G, C*A, T*G, C*A, T*C, C*T and G*T.

The dimethoxytrityl group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed 6 hours to go to completion. The supernatant containing the oligomer was then removed from the support and the support was rinsed twice with 1 ml of 1/1 acetonitrile/water; the washings were combined with the supernatant. The combined solution was diluted to 30 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column it was washed with 5 ml of water. The product was then eluted with 2 ml of 1/1 acetonitrile/water.

Example L

Preparation of 5'-(G*A)-(G*G)-(A*G)-(GA)-(G*G)-(A*G)-(G*A)-(A*G)-G-3' [SEQ. ID. NO. 17] Having Repeated MP($R_p$)/MP Linkage Structures The grouped dinucleosides indicate the coupled dimers and the asterisks indicates where the stereochemistry is fixed (chirally defined or chirally pure) as the fast eluting dimer isomer on silica gel (identified as $R_p$).

This oligomer was prepared using automated synthesis coupling G*A, G*G and A*G MP($R_p$)/MP dimer synthons prepared according to the procedures of Examples A1 and A3.

An amount of G*A, G*G and A*G dimer synthons was dissolved in acetonitrile to give a concentration of 0.1M and stored over 3 Å molecular sieves (Millipore, Milford, Mass.) overnight.

The dissolved dimers, with molecular sieves, were placed in conical vessels on a Millipore Expedite DNA Synthesizer which as equipped with end-line filters to remove particulates. All other reagents (oxidizer, deblock, capping reagents and activator) were prepared and applied to the appropriate positions on the instrument as instructed in the manual. The coupling program was modified to place the oxidizing step immediately subsequent to the coupling step in order to reduce backbone cleavage prior to oxidation. (See Hogrefe, R. I., et al. "An Improved Method for the Synthesis and Deprotection of Methylphosphonate oligonucleotides" in *Methods in Molecular Biology*, vol. 20: *Protocols for oligonucleotides and Analoas* (ed. Agrawal, S.) pages 143–164, Humana Press, Totowa, N.Y. (1983). The programming parameters for one synthesis cycle ("Syn4all-1 µmol") are set forth in I of U.S. patent application Ser. No. 08/154,013.

A 1 µmole scale DNA synthesis column (Millipore) was filled with 1 µmol of methacrylate support-bound deoxyguanosine and was placed on the DNA synthesizer. The dimers were coupled sequentially from the 3' terminus. The dimethoxytrityl protecting group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed 6 hours to go to completion. The supernatant containing the oligomer was then removed from the support and the support rinsed twice with 1 ml of 1/1 acetonitrile/water, when combined with the supernatant. The combined solution was diluted to 50 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column, it was washed with 5 ml of water. The product was then eluted with 1.8 ml of 1/1 acetonitrile/water.

The crude yield was 87 OD$_{260}$ units. The Oligomers was purified on HPLC using a β-cyclobond standard phase 4.5×250 mm column (Azetec, Inc. Whippany, N.J.) with a decreasing gradient (80% to 40%) of acetonitrile in 0.05M triethylammonium acetate (pH 7). The isolated yield was 22 $OD_{260}$ units (25%). The product was characterized by electron spray mass spectrometry (calc. 5407/found 5401).

Example M

Preparation of an Oligomer Having Alternating MP $(R_p)$/PS Internucleosidyl Linkages An oligomer having alternating MP($R_4$)/PS internucleosidyl linkages is prepared using dimer synthons. All the parameters of the synthesis, deprotection and purification are as described in Example H, except that the oxidizing reagent is replaced by a 0.1M solution of 3H-1,2-benzodithiole-3-one, 1,1-dioxide or a 0.1M solution of sulfur in 1/1 carbon disulfide/diisopropylethylamine.

Example N

Preparation of an Oligomer Having Alternating MPS($R_p$)/DE Internucleosidyl Linkages An oligomer having alternating MPS($R_p$)/DE internucleosidyl linkages is prepared using the dimer synthons of Example D. All other parameters of synthesis, deprotection and purification are as described in Example H.

Example O

Preparation of an Oligomer Having Alternating MPS($R_p$)/PS Internucleosidyl Linkages An oligomer having alternating MPS($R_p$)/PS internucleosidyl linkages is prepared using the dimer synthons of Example D. All of the parameters of synthesis, deprotection and purification are as described in Example H, except that the oxidizing reagent is replaced by a 0.1M solution of 3H-1,2-benzo-dithiole-3-one, 1,1-dioxide or a 0.1M solution of sulfur in 1/1 carbon disulfide/diisopropylethylamine.

Example P

Preparation of an Oligomer Having Alternating MP $(R_p)$/PS2 Internucleosidyl Linkages An oligomer having alternating MP($R_p$)/PS2 internucleosidyl linkages is prepared using the dimer synthons of Example E. All of the parameters of synthesis, deprotection and purification are as described in Example O.

Example Q

Preparation of an Oligomer Having Alternating MPS($R_p$)/PS2 Internucleosidyl Linkages An oligomer having alternating MPS($R_4$)/PS2 internucleosidyl linkages is prepared using the dimer synthons of Example F. All of the parameters of synthesis, deprotection and purification are as described in Example P.

Example Q1

Preparation of an Oligomer Having Alternating MP $(R_p)$/2'-O-Methyl DE Internucleosidyl Linkages An oligomer having alternating MP($R_p$)/2'-O-Methyl DE internucleosidyl linkages is prepared using dimer synthons similar to those of Example G. All other parameters of synthesis, deprotection and purification are as described in Example I.

Example R

Preparation of an Oligomer Having Alternating MP $(R_p)$/MPS Internucleosidyl Linkages The preparation of an oligomer having alternating MP($R_4$)/MPS internucleosidyl linkages is accomplished using dimer synthons prepared according to Examples A1 and A3 and dissolved and stored over molecular sieves. The oxidizing reagent is a 0.1M solution of 3H-1,2-benzodithiole-3-one, 1,1-dioxide ("Beaucage Reagent", See, Iyer, R. P. et al., JACS 112:1254–1255 (1990)) or a 0.1M solution of sulfur in 1/1 carbon disulfide/diisopropylethylamine, with synthesis proceeding generally as described in Example L.

Example S

Preparation of an Oligomer Having 2'-O-Methyl Nucleosidyl Units and Alternating MP($R_p$)/MPS Internucleosidyl Linkages This oligomer is prepared using the dimer synthons as described in Examples B1–B4 and B6 and following the general synthetic procedures of Example 8 of U.S. patent application Ser. No. 08/154,013, except that the oxidizing reagent described therein is a 0.1M solution of 3H-1,2-benzodithiole-3-one, 1,1-dioxide or a 0.1M solution on 1/1 carbon disulfide/diisopropylamine.

Example T

Preparation of an Oligomer Having 2'-O-Methyl Nucleosidyl Units and Alternating MPS($R_p$)/MP Internucleosidyl Linkages This oligomer is prepared using dimer synthons as described in Example C above and by following the parameters of synthesis, deprotection and purification of Example S.

Example U

Preparation of an Oligomer Having Alternating MPS($R_p$)/MP Internucleosidyl Linkages This oligomer is prepared using dimer synthons prepared according to Examples A1 and A3, substituting Beaucage reagent for the oxidizer in Example A1, and by following the parameters of synthesis, deprotection and purification as described above in Example L.

Example V

Preparation of an Oligomer Having Alternating MPS($R_p$)/MPS Internucleosidyl Linkages This oligomer is prepared using dimer synthons as referred to in Example U and by following the parameters of synthesis, deprotection and purification as described above in Example L, except that the oxidizing reagent used therein is replaced by a 0.1M solution of 3H-1,2-benzodithiole, 1,1-dioxide or a 0.1M solution of sulfur in 1/1 carbon disulfide/ diisopropylethylamine.

Example W

Preparation of 2'-F Dimer Synthons

Dimer synthons useful in the preparation of the oligomers of the present invention may be prepared using 2'-fluoronucleosides. Methods for preparation of 2'-fluoronucleosides have been reported and are known to those skilled in the art. (See, e.g.: Codington, JOC Vol. 29 (1964) (2'-F U); Mangel, Angew. Chem. 96:557–558 (1978) and Doen, JOC 32:1462–1471 (1967) (2'-F C); Ikehara, Chem. Pharm. Bull. 29:1034–1038 (1981) (2'-F G); Ikehara, J. Carbohydrates, Nucleosides, Nucleotides 7:131–140 (1980) (2'-F A), and also Krug, A, Nucleosides & Nucleotides 8:1473–1483 (1989).

The preparation of dimer synthons using 2'-fluoronucleosides may be accomplishing using the procedures analogous to those described for the 2'-O-methyl dimer synthons (See, e.g., Examples B, C, and G). The resulting dimer synthons may be used to prepare oligomers using methods analogous to the methods used for the 2'O-methyl dimer synthons such as in Example I.

Example X

Preparation of $MP(R_p)/MP(R_p)/DE$ and $MP(R_p)/MP(R_p)/MP$ Trimer Synthons

The above-identified trimer synthons are prepared using the $MP(R_p)/MP$ dimer synthons of Example A3. The dimer synthon is coupled to a 5'-hydroxy, 3'-silylated nucleoside according to the methods of Example 1A for the coupling of the 3'-nucleoside to the monomer phosphoramidite.

The selected 5'-hydroxy, 3'-silylated nucleoside (1 equivalent) and isomerically pure $R_p$ dimer methylphosphonamide (1.25 equivalents) are weighed into a round bottom flask and dried by co-evaporation with acetonitrile. The resulting foam is dissolved in acetonitrile and treated with a solution of 0.45M tetrazole in acetonitrile (4.5 equivalents). After 3 minutes, the reaction mixture is oxidized and the reaction product is worked up as described in Example 1A. The diastereoisomers of the 3'-silylated trimer are resolved on a silica gel column as described in Example 1A for resolution of the dimer isomers. The configuration of the separated diastereoisomers is determined using 2-D nmr (ROSEY). The trimer having the desired chiral configuration ($R_p/R_p$) of the two internucleosidyl linkages is converted to a trimer synthon by reaction with chloro-β-cyanoethoxy-N,N-diisopropylaminophosphoramidite using methods as described in Example A2. The trimer synthon is worked up and purified using methods as described in Example 1B to achieve the $MP(R_p)/MP(R_p)/DE$ trimer.

Using similar procedures, an $MP(R_p)/MP(R_p)/MP$ phosphoramidite synthon may be obtained by using chloromethyl-N,N-diisopropylaminophosphine in the final reaction as described in Example A3 for the corresponding dimer synthon. Workup and purification are as described in Example A3.

Example Y

Preparation of 2'-O-Allyl Dimer and Trimer Synthons and Their Use in Oligomer Synthesis The dimer and trimer synthons described, for example, in Examples A and X can be prepared using 2'-O-allyl nucleosides. The preparation of 2'-O-allyl nucleosides and their use in the preparation of oligomers has been reported (see e.g. Iribarren, et al. (1990) *Proc. Natl. Acad. Sci. (USA)* 87:7747–51; and Lesnik et al. (1983), *Biochemistry* 32:7832–8), and such substituted nucleosides are commercially available. The nucleosides are used to prepare dimer and trimer synthons using procedures described hereinabove. The synthons are used to prepare oligomers using methods such as those described in Examples J, K, L, M and others above.

Example Z

Preparation of an Oligomer Having $MP(R_p)/MP/DE$ Internucleosidyl Linkages

The above-identified oligomer is prepared using the trimer synthons of Example X, or by those in Example 20 of U.S. patent application Ser. No. 08/154,014, and by following the methods described in Example H, substituting the trimer synthons for dimer synthons. All other parameters of synthesis, deprotection and purification are as described in Example H.

Example AA

Preparation of an Oligomer Having $MP(R_p)/MP(R_p)/MP$ Internucleosidyl Linkages The above-identified oligomer is prepared using the procedures described in Example 14 of U.S. patent application Ser. No. 08/154,013.

Example AB

Preparation of Racemic Methylphosphonate Oligonucleotides

Various racemic oligomers were synthesized using 5'-(dimethoxytrityl) deoxynucleoside-3'-[(N,N-diisopropylamino)methyl]-phosphonoamidite monomers. Solid-phase synthesis was performed on methacrylate polymer supports with a Biosearch Model 8750 DNA synthesizer according to the manufacturer's recommendations except for the following modifications: the monomers were dissolved in acetonitrile at a concentrations of 100 mM, except dG, which was dissolved in 1/1 acetonitrile/dichloromethane at 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A=10% acetic anhydride in acetonitrile. CAP B=0.625% N,N-dimethylaminopyridine in pyridine.

The dimethoxytrityl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/$NH_4OH$ (9/9/1). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when combined with the supernatant. The combined solution was diluted to 30 ml total volume with water and neutralized with approximately 4 ml of 6N HCl. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column it was washed with 30 ml of water. The product was then eluted with 5 ml of 1/1 acetonitrile/water.

Example AC

Chimeric Oligonucleotide Assembly From $MP(R_p)/MP$ and $MP(R_p)/DE$ Dimer Synthons and Phosphoramidite and Methylphosphonamidite Monomer Synthons $MP(R_4)/MP$ dimer synthons contained a methylphosphoramidite coupling group at the 3' end. When coupled together to make an oligomer, these synthons give racemic methylphosphonate linkages at every other position.

$R_p$-MP/-DE dimer synthons contained a β-cyanoethyl phosphoramidite coupling group at the 3'-end. Both types of dimer synthons were synthesized as described in Example 1. Methylphosphonamidite monomer synthons were synthesized at JBL Scientific (San Luis Obispo, Calif.). Betacyanoethyl phosphoramidite monomer synthons were purchased from Milligen/Biosearch.

All synthons were coupled using a Milligen Expedite™ automated DNA synthesizer. The coupling programs for each synthon were as tabulated below. To generate a phosphorothioate bond during a coupling step, the program "Thioate-5 μM" was used with either a dimer or monomer synthon containing a β-cyanoethyl phosphoramidite coupling group.

DIESTER - 5 μM

| Function | Mode | Amount /Arg1 | Time(sec) /Arg2 | Description |
|---|---|---|---|---|
| $Deblocking | | | | |
| 144 /* Advance Frac */ | NA | 1 | 0 | "Event out ON" |
| 0 /* Default */ | WAIT | 0 | 1.5 | "Wait" |
| 141 /* Photometer S */ | NA | 1 | 1 | "START data collection" |
| 16 /* Dblk */ | PULSE | 10 | 0 | "Dblk to column" |
| 16 /* Dblk */ | PULSE | 200 | 49 | "Deblock" |
| 36 /* Wsh A to Cl */ | PULSE | 60 | 0 | "Flush system with Wsh A" |
| 141 /* Photometer S */ | NA | 0 | 1 | "STOP data collection" |
| 39 /* Gas A to Cl */ | PULSE | 10 | 0 | "Gas A to Cl waste" |
| 144 /* Advance Frac */ | NA | 2 | 0 | "Event out OFF" |
| 12 /* Wsh A */ | PULSE | 200 | 0 | "Wsh A" |
| $Coupling | | | | |
| 1 /* Wsh */ | PULSE | 10 | 0 | "Flush system with Wsh" |
| 2 /* Act */ | PULSE | 10 | 0 | "Flush system with Act" |
| 18 /* A + Ac */ | PULSE | 5 | 0 | "Monomer + Ac to column" |
| 18 /* A + Ac */ | PULSE | 16 | 60 | "Couple monomer" |
| 2 /* Act */ | PULSE | 3 | 10 | "Couple monomer" |
| 1 /* Wsh */ | PULSE | 7 | 56.1 | "Couple monomer" |
| 1 /* Wsh */ | PULSE | 50 | 0 | "Flush system with Wsh" |
| $Capping | | | | |
| 13 /* Caps */ | PULSE | 25 | 0 | "Caps to column" |
| 12 /* Wsh A */ | PULSE | 50 | 0 | "Wsh A" |
| 12 /* Wsh A */ | PULSE | 150 | 0 | "End of cycle wash" |
| $Oxidizing | | | | |
| 15 /* Ox */ | PULSE | 50 | 30 | "Ox" |
| 12 /* Wsh A */ | PULSE | 50 | 0 | "Flush system with Wsh A" |
| $Capping | | | | |
| 13 /* Caps */ | PULSE | 25 | 0 | "Caps to column" |
| 12 /* Wsh A */ | PULSE | 50 | 0 | "Wsh A" |
| 12 /* Wsh A */ | PULSE | 150 | 0 | "End of cycle wash" |

THIOATE - 5 μM

| Function | Mode | Amount /Arg1 | Time(sec) /Arg2 | Description |
|---|---|---|---|---|
| $Deblocking | | | | |
| 144 /* Advance Frac */ | NA | 1 | 0 | "Event out ON" |
| 0 /* Default */ | WAIT | 0 | 1.5 | "Wait" |
| 141 /* Photometer S */ | NA | 1 | 1 | "START data collection" |
| 16 /* Dblk */ | PULSE | 10 | 0 | "Dblk to column" |
| 16 /* Dblk */ | PULSE | 200 | 49 | "Deblock" |
| 38 /* Wsh A to Cl */ | PULSE | 80 | 0 | "Flush system with Wsh A" |
| 141 /* Photometer S */ | NA | 0 | 1 | "STOP data collection" |
| 39 /* Gas A to Cl */ | PULSE | 10 | 0 | "Gas A to Cl waste" |
| 144 /* Advance Frac */ | NA | 2 | 0 | "Event out OFF" |
| 12 /* Wsh A */ | PULSE | 200 | 0 | "Wsh A" |
| $Coupling | | | | |
| 1 /* Wsh */ | PULSE | 10 | 0 | "Flush system with Wsh" |
| 2 /* Act */ | PULSE | 10 | 0 | "Flush system with Act" |
| 23 /* 6 + Act */ | PULSE | 6 | 0 | "Monomer + Act to column" |
| 23 /* 6 + Act */ | PULSE | 17 | 60 | "Couple monomer" |
| 2 /* Act */ | PULSE | 4 | 10 | "Couple monomer" |

-continued

THIOATE - 5 μM

| Function | Mode | Amount /Arg1 | Time(sec) /Arg2 | Description |
|---|---|---|---|---|
| 1 /* Wsh */ | PULSE | 7 | 55.9 | "Couple monomer" |
| 1 /* Wsh */ | PULSE | 50 | 0 | "Flush system with Wsh" |
| $Capping | | | | |
| 13 /* Caps */ | PULSE | 25 | 0 | "Caps to column" |
| 12 /* Wsh *A */ | PULSE | 50 | 0 | "Wsh A" |
| 12 /* Wsh A */ | PULSE | 150 | 0 | "End of cycle wash" |
| $Oxidizing | | | | |
| 17 /* Aux */ | PULSE | 5 | 0 | "SOx" |
| 17 /* Aux */ | PULSE | 45 | 60 | "SOx" |
| 12 /* Wsh A */ | PULSE | 50 | 0 | "Flush system with Wsh A" |
| $Capping | | | | |
| 13 /* Caps */ | PULSE | 25 | 0 | "Caps to column" |
| 12 /* Wsh A */ | PULSE | 50 | 0 | "Wsh A" |
| 12 /* Wsh A */ | PULSE | 150 | 0 | "End ot cycle wash" |

METHYLPHOSPHONATE - 5 μM

| Function | Mode | Amount /Arg1 | Time(sec) /Arg2 | Description |
|---|---|---|---|---|
| $Deblocking | | | | |
| 144 /* Advance Frac */ | NA | 1 | 0 | "Event out ON" |
| 0 /* Default */ | WAIT | 0 | 1.5 | "Wait" |
| 141 /* Photometer S */ | NA | 1 | 1 | "START data collection" |
| 16 /* Dblk */ | PULSE | 10 | 0 | "Dblk to column" |
| 16 /* Dblk */ | PULSE | 200 | 49 | "Deblock" |
| 38 /* Wsh A to Cl */ | PULSE | 80 | 0 | "Flush system with Wsh A" |
| 141 /* Photometer S */ | NA | 0 | 1 | "STDP data collection" |
| 39 * Gas A to Cl */ | PULSE | 10 | 0 | "Gas A to Cl waste" |
| 144 /* Advance Frac */ | NA | 2 | 0 | "Event out OFF" |
| 12 /* Wsh A */ | PULSE | 200 | 0 | "Wsh A" |
| $Coupling | | | | |
| 1 /* Wsh */ | PULSE | 10 | 0 | "Flush system with Wsh" |
| 2 /* Act */ | PULSE | 10 | 0 | "Flush system with Act" |
| 18 /* A + Act */ | PULSE | 5 | 0 | "Monomer + Act to column" |
| 18 /* A + Act */ | PULSE | 16 | 60 | "Couple monomer" |
| 2 /* Act */ | PULSE | 3 | 10 | "Couple monomer" |
| 1 /* Wsh */ | PULSE | 7 | 56.1 | "Couple monomer" |
| 1 /* Wsh */ | PULSE | 50 | 0 | "Flush system with Wsh" |
| $Oxidizing | | | | |
| 15 /* Qx */ | PULSE | 50 | 30 | "Ox" |
| 12 /* Wsh A */ | PULSE | 50 | 0 | "Flush system with Wsh A" |
| $Capping | | | | |
| 13 /* Caps */ | PULSE | 25 | 0 | "Caps to column" |
| 12 /* Wsh A */ | PULSE | 50 | 0 | "Wsh A" |
| 12 /* Wsh A */ | PULSE | 150 | 0 | "End of cycle wash" |

MP($R_p$)/MP - 5 μM

| Function | Mode | Amount /Arg1 | Time(sec) /Arg2 | Description |
|---|---|---|---|---|
| $Deblocking | | | | |
| 144 /* Advance Frac */ | NA | 1 | 0 | "Event out ON" |
| 0 /* Default */ | WAIT | 0 | 1.5 | "Wait" |
| 141 /* Photometer S */ | NA | 1 | 1 | "START data collection" |
| 16 /* Dblk */ | PULSE | 10 | 0 | "Dblk to column" |
| 16 /* Dblk */ | PULSE | 200 | 49 | "Deblock" |
| 38 /* Wsh A to Cl */ | PULSE | 80 | 0 | "Flush system with Wsh A" |
| 141 /* Photometer S */ | NA | 0 | 1 | "STDP data collection" |

-continued

MP($R_p$)/MP - 5 μM

| Function | | Mode | Amount /Arg1 | Time(sec) /Arg2 | Description |
|---|---|---|---|---|---|
| 39 /* Gas A to Cl | */ | PULSE | 10 | 0 | "Gas A to Cl waste" |
| 144 /* Advance Frac | */ | NA | 2 | 0 | "Event out OFF" |
| 12 /* Wsh A | */ | PULSE | 200 | 0 | "Wsh A" |
| $Coupling | | | | | |
| 1 /* Wsh | */ | PULSE | 10 | 0 | "Flush system with Wsh" |
| 2 /* Act | */ | PULSE | 10 | 0 | "Flush system with Act" |
| 18 /* A + Act | */ | PULSE | 5 | 0 | "Monomer + Act to column" |
| 18 /* A + Act | */ | PULSE | 18 | 60 | "Couple monomer" |
| 2 /* Act | */ | PULSE | 3 | 10 | "Couple monomer" |
| 1 /* Wsh | */ | PULSE | 7 | 56.1 | "Couple monomer" |
| 1 /* Wsh | */ | PULSE | 50 | 0 | "Flush system with Wsh" |
| $Oxidizing | | | | | |
| 15 /* Ox | */ | PULSE | 50 | 30 | "Ox" |
| 12 /* Wsh A | */ | PULSE | 50 | 0 | "Flush system with Wsh A" |
| $Capping | | | | | |
| 13 /* Caps | */ | PULSE | 25 | 0 | "Caps to column" |
| 12 /* Wsh A | */ | PULSE | 50 | 0 | "Wsh A" |
| 12 /* Wsh A | */ | PULSE | 150 | 0 | "End of cycle wash" |

MP($R_p$)/DE - 5 μM

| Function | | Mode | Amount /Arg1 | Time(sec) /Arg2 | Description |
|---|---|---|---|---|---|
| $Deblocking | | | | | |
| 144 /* Advance Frac | */ | NA | 1 | 0 | "Event out ON" |
| 0 /* Default | */ | WAIT | 0 | 1.5 | "Wait" |
| 141 /* Photometer S | */ | NA | 1 | 1 | "START data collection" |
| 16 /* Dblk | */ | PULSE | 10 | 0 | "Dblk to column" |
| 16 /* Dblk | */ | PULSE | 200 | 49 | "Deblock" |
| 38 /* Wsh A to Cl | */ | PULSE | 80 | 0 | "Flush system with Wsh A" |
| 141 /* Photometer S | */ | NA | 0 | 1 | "STDP data collection" |
| 39 /* Gas A to Cl | */ | PULSE | 10 | 0 | "Gas A to Cl waste" |
| 144 /* Advance Frac | */ | NA | 2 | 0 | "Event out OFF" |
| 12 /* Wsh A | */ | PULSE | 200 | 0 | "Wsh A" |
| $Coupling | | | | | |
| 1 /* Wsh | */ | PULSE | 10 | 0 | "Flush system with Wsh" |
| 2 /* Act | */ | PULSE | 10 | 0 | "Flush system with Act" |
| 18 /* A + Act | */ | PULSE | 5 | 0 | "Monomer + Act to column" |
| 18 /* A + Act | */ | PULSE | 18 | 60 | "Couple monomer" |
| 2 /* Act | */ | PULSE | 3 | 10 | "Couple monomer" |
| 1 /* Wsh | */ | PULSE | 7 | 56.1 | "Couple monomer" |
| 1 /* Wsh | */ | PULSE | 50 | 0 | "Flush system with Wsh" |
| $Oxidizing | | | | | |
| 17 /* Aux | */ | PULSE | 50 | 30 | "Aux" |
| 12 /* Wsh A | */ | PULSE | 50 | 0 | "Flush system with Wsh A" |
| $Capping | | | | | |
| 13 /* Caps | */ | PULSE | 25 | 0 | "Caps to column" |
| 12 /* Wsh A | */ | PULSE | 50 | 0 | "Wsh A" |
| 12 /* Wsh A | */ | PULSE | 150 | 0 | "End of cycle wash" |

Applying one or more of these coupling routines with the appropriate dimer or monomer synthons, one skilled in the art can recognize that each of the chimeric oligomers described in subsequent examples can be synthesized.

Deprotection and purification of each chimeric oligomer was done essentially as described in Examples H through L.

The identities of certain chimeric oligomers made according to this Example, as well as other compounds, were confirmed by electrospray mass spectrometry.

We claim:

1. A process for separating an oligomer having a selected nucleoside sequence from an oligomer impurity having a different nucleoside sequence which comprises normal phase column chromatography on a column having a support selected from polyhydroxyethyl aspartamide, silica, and hydrophilic silica, wherein said hydrophilic silica comprises silica which is modified with an uncharged hydroxylated hydrophilic moiety other than cydodextrin, including separation conditions selected so that said oligomer has a different retention time on said column than said oligomer impurity, provided that said oligomer and said oligomer impurity differ in nucleoside sequence by other than a thymine or uracil base.

2. The process of claim 1, wherein said oligomer is substantially neutral wherein at least about 80 percent of internucleosidyl linkages between nucleoside monomers are nonionic.

3. A process according to claim 2, wherein the oligomer is a methylphosphonate oligomer.

4. A process according to claim 3, wherein said oligomer has internucleosidyl linkages which are all methylphosphonate linkages or has a 5'-diester linkage and the remainder of linkages are methylphosphonate linkages.

5. A process according to claim 1, wherein said oligomer has internucleosidyl linkages selected from the group consisting of phosphodiester, phosphorothioate, phosphorodithioate, methylphosphonothioate, and methylphosphonate internucleosidyl linkages.

6. A process according to claim 5 wherein said oligomer has methylphosphonate or methylphosphonothioate internucleosidyl linkages which are mixed with non-phosphonate internucleosidyl linkages selected from the group consisting of phosphodiester, phosphorothioate and phosphorodithioate linkages.

7. A process according to claim 6 wherein said methylphosphonate or methylphosphonothioate linkages and said non-phosphonate linkages are interspersed in a ratio of from 1 non-phosphonate linkage to about 1 methylphosphonate or methylphosphonothioate linkage to 1 non-phosphonate linkage to about 4 methylphosphonate or methylphosphonothioate linkages.

8. A process according to claim 7 wherein said methylphosphonate or methylphosphonothioate linkages and said non-phosphonate linkages alternate.

9. A process according to claim 5 wherein said oligomer has about 5 to about 9 consecutive non-phosphonate internucleosidyl linkages selected from the group consisting of phosphodiester, phosphorothioate sand phosphorodithioate linkages.

10. A process according to claim 9 wherein said oligomer has at least one methylphosphonate or methylphosphonothioate internucleosidyl linkage.

11. A process according to claim 1, wherein the retention time of the oligomer corresponds to a capacity factor (k') greater than 5, as calculated according to relationships (1) $(k'=(t_r-t_o)/t_o)$ and (2) $(t_r=(k')(t_o)+(t_o))$ wherein $t_r$ is retention time and $t_o$ is column dead time.

12. A process according to claim 11, wherein the retention time of the oligomer corresponds to a capacity factor (k') between 5 and 10.

13. A process according to claim 1 wherein said hydrophilic moiety is selected from, glucose, glycidoxypropyl and diol groups.

14. A process according to claim 1, wherein said silica has a surface area greater than 100 m$^2$/g and a pore diameter greater than 8 nm.

15. A process according to claim 14, wherein said silica has a surface between 100 and 400 m$^2$/g.

16. A process according to claim 14, further comprising a mobile phase comprising acetonitrile and aqueous buffer in proportions of 30–70% acetonitrile to 70–30% aqueous buffer.

17. A process according to claim 16, wherein said aqueous buffer has a pH of about 4–8 and an ion concentration of about 2 to about 100 mM.

18. A process according to claim 16, wherein said column is run at a temperature of 30°–70° C., and said aqueous buffer has a pH of 4–8 and an ion concentration of 2–100 mM.

19. A process according to claim 1 further comprising a mobile phase comprising acetonitrile and aqueous buffer.

20. A process according to claim 1, further comprising reverse phase chromatography of the separated oligomer.

21. A process according to claim 1 wherein said internucleosidyl linkages are selected from phosphodiester and methylphosphonate linkages and the nucleosides of the oligomer have 2'-O-methylribosyl groups.

22. A process according to claim 1 wherein said oligomer impurity has fewer nucleosides than the oligomer.

23. A process according to claim 22 wherein said oligomer impurity is a failure sequence.

24. A process according to claim 1 wherein said oligomer is a conjugate between an oligonucleoside and a conjugation partner.

25. A process according to claim 24 wherein said oligomer is a neutral oligomer.

26. A process according to claim 24, wherein said oligomer has internucleosidyl linkages selected from the group consisting of phosphodiester, phosphorothioate, phosphorodithioate, methylphosphonothioate, and methylphosphonate internucleosidyl linkages.

27. A process according to claim 26 wherein said oligomer has methylphosphonate or methylphosphonothioate internucleosidyl linkages which are mixed with non-phosphonate internucleosidyl linkages selected from the group consisting of phosphodiester, phosphorothioate and phosphorodithioate linkages.

28. A process according to claim 27 wherein said methylphosphonate or methylphosphonothioate linkages and said non-phosphonate linkages are interspersed in a ratio of from 1 non-phosphonate linkage to about 1 methylphosphonate linkage to 1 non-phosphonate linkage to about 4 methylphosphonate or methylphosphonothioate linkages.

29. A process according to claim 28 wherein said methylphosphonate or methylphosphonothioate linkages and said non-phosphonate linkages alternate.

30. A process according to claim 26 wherein said oligomer has about 5 to about 9 consecutive non-phosphonate internucleosidyl linkages selected from the group consisting of phosphodiester, phosphorothioate sand phosphorodithioate linkages.

31. A process according to claim 30 wherein said oligomer has at least one methylphosphonate or methylphosphonothioate internucleosidyl linkage.

\* \* \* \* \*

UNITED STATES PATENT AND TRADEMARK OFFICE
CERTIFICATE OF CORRECTION

PATENT NO. : 5,811,538
DATED : September 22, 1998
INVENTOR(S) : Timothy Andrew Riley; Mark Alan Reynolds; Lloyd Robert Snyder; Robert E. Klem It is certified that error appears in the above-identified patent and that said Letters Patent is hereby corrected as shown below:

Claim 13,
Please delete [, glucose, glycidoxypropyl and diol groups].

Please add -- glucose and glycidoxypropyl --.

Signed and Sealed this

Fourth Day of December, 2001

Attest:

NICHOLAS P. GODICI
Attesting Officer
Acting Director of the United States Patent and Trademark Office

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CTCTCTCTCT CTCTA                                        15

( 2 ) INFORMATION FOR SEQ ID NO: 2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CUCUCUCUCU CUCUA                                        15

( 2 ) INFORMATION FOR SEQ ID NO: 3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

TAGCTTCCTT AGCTCCTGC                                  19

( 2 ) INFORMATION FOR SEQ ID NO: 4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GTCTTCCATG CATGTTGTC                                  19

( 2 ) INFORMATION FOR SEQ ID NO: 5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TGGCCATGGC AGCTG                                        15

( 2 ) INFORMATION FOR SEQ ID NO: 6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (xi) SEQUENCE DESCRIPTION: SEQ ID NO: 6:

GTCTTTGAAC TCTGCTTA                          18

(2) INFORMATION FOR SEQ ID NO: 7:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO: 7:

GCTTTTGAAC TCTGCTTA                          18

(2) INFORMATION FOR SEQ ID NO: 8:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO: 8:

CAUGACCGCA CCACGCUC                          18

(2) INFORMATION FOR SEQ ID NO: 9:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO: 9:

UUCCUCCUGC GG                                12

(2) INFORMATION FOR SEQ ID NO: 10:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO: 10:

CUCUCUCUCU CUCUCT                            16

(2) INFORMATION FOR SEQ ID NO: 11:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO: 11:

GTCTTCCTGC CCCATTGC                          18

(2) INFORMATION FOR SEQ ID NO: 12:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO: 12:

```
GGUAUAUCCA  GUGAUCUUCU  UCTC                                                          24
```

( 2 ) INFORMATION FOR SEQ ID NO: 13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 13:

```
GCCGGTACCT  GCTTGACAAG                                                                20
```

( 2 ) INFORMATION FOR SEQ ID NO: 14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 14:

```
TAGCTTCCTT  AGCTCCTG                                                                  18
```

( 2 ) INFORMATION FOR SEQ ID NO: 15:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 15:

```
CUUGGCUATT  GCTTCCAUCU  T                                                             21
```

( 2 ) INFORMATION FOR SEQ ID NO: 16:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 16:

```
GTCTTCCATG  GATGTTGT                                                                  18
```

( 2 ) INFORMATION FOR SEQ ID NO: 17:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 17:

```
GAGGAGGAGG  AGGAAGG                                                                   17
```